US012670987B2

(12) United States Patent
Gumbel et al.

(10) Patent No.: US 12,670,987 B2
(45) Date of Patent: *Jun. 30, 2026

(54) CARE PROVIDER COVERAGE FILTER FOR COMMUNICATION DEVICES

(71) Applicant: Stryker Corporation, Kalamazoo, MI (US)

(72) Inventors: Matthew J. Gumbel, Angola, IN (US); David Holscher, Fort Wayne, IN (US); Arun Mirchandani, Pleasanton, CA (US)

(73) Assignee: Stryker Corporation, Portage, MI (US)

( * ) Notice: Subject to any disclaimer, the term of this patent is extended or adjusted under 35 U.S.C. 154(b) by 46 days.

This patent is subject to a terminal disclaimer.

(21) Appl. No.: 18/674,222

(22) Filed: May 24, 2024

(65) Prior Publication Data

US 2024/0312611 A1 Sep. 19, 2024

Related U.S. Application Data

(63) Continuation of application No. 17/024,084, filed on Sep. 17, 2020, now Pat. No. 12,027,256.

(51) Int. Cl.
G16H 40/20 (2018.01)
G06Q 10/1093 (2023.01)
(Continued)

(52) U.S. Cl.
CPC ......... G16H 40/20 (2018.01); G06Q 10/1093 (2013.01); G16H 40/67 (2018.01); H04W 4/08 (2013.01); H04W 4/12 (2013.01)

(58) Field of Classification Search
USPC ....................................................... 705/2–3
See application file for complete search history.

(56) References Cited

U.S. PATENT DOCUMENTS 5,576,952 A 11/1996 Stutman et al.
7,034,691 B1 4/2006 Rapaport et al.
(Continued)

FOREIGN PATENT DOCUMENTS

GB 2517259 11/2014
JP 2004110186 4/2004
(Continued)

OTHER PUBLICATIONS

C.-Y. Chiang et al., "Pervasive Communications for Care Professionals in Hospitals," 2008 2nd International Conference on Bioinformatics and Biomedical Engineering, Shanghai, China, 2008, pp. 1351-1354, doi: 10.1109/ICBBE.2008.667. (Year: 2008).*
(Continued)

*Primary Examiner* — Bennett Stephen Erickson
(74) *Attorney, Agent, or Firm* — McDonnell Boehnen Hulbert & Berghoff LLP

(57) ABSTRACT

Embodiments include methods, devices, systems, and non-transitory process-readable storage media for managing care provider coverage in a medical communication system. Some embodiments may include receiving from a first communication device associated with a first user a coverage request defining a coverage period and requesting that a second user associated with a second communication device provide care coverage for the first user, sending a notification of the coverage request to the second communication device including the coverage period and requesting agreement to provide care coverage for the first user, receiving from the second communication device an acceptance of the coverage request, and directing to the second communication device a message sent to the first communication device during the coverage period in response to receiving the acceptance of the coverage request.

20 Claims, 19 Drawing Sheets

(51) Int. Cl.
| | |
|---|---|
| *G16H 40/67* | (2018.01) |
| *H04W 4/08* | (2009.01) |
| *H04W 4/12* | (2009.01) |

(56) References Cited

U.S. PATENT DOCUMENTS

| | | | | |
|---|---|---|---|---|
| 9,149,190 | B2 | 10/2015 | Mayoras, Jr. | |
| 9,652,960 | B2 | 5/2017 | Flinsenberg et al. | |
| 9,740,825 | B2 | 8/2017 | Sansale et al. | |
| 10,025,905 | B2 | 7/2018 | Dantsker et al. | |
| 10,057,732 | B2 | 8/2018 | Soomro | |
| 10,153,994 | B2 | 12/2018 | Mancine et al. | |
| 11,257,572 | B1 | 2/2022 | Narke et al. | |
| 11,348,681 | B1* | 5/2022 | Morrow | G16H 10/60 |
| 2005/0071190 | A1 | 3/2005 | Herger et al. | |
| 2007/0067185 | A1 | 3/2007 | Halsted | |
| 2007/0083403 | A1 | 4/2007 | Baldwin et al. | |
| 2007/0168223 | A1 | 7/2007 | Fors et al. | |
| 2008/0114689 | A1 | 5/2008 | Psynik et al. | |
| 2012/0136221 | A1 | 5/2012 | Killen et al. | |
| 2012/0191466 | A1 | 7/2012 | Quint et al. | |
| 2012/0290311 | A1 | 11/2012 | Tara et al. | |
| 2014/0081667 | A1* | 3/2014 | Joao | G16H 40/63 |
| | | | | 705/3 |
| 2014/0180715 | A1* | 6/2014 | Phillips | G06Q 10/103 |
| | | | | 705/2 |
| 2014/0244277 | A1 | 8/2014 | Krishna Rao et al. | |
| 2014/0278650 | A1 | 9/2014 | Bagheri et al. | |
| 2015/0286787 | A1 | 10/2015 | Chen et al. | |
| 2016/0117464 | A1 | 4/2016 | Ito et al. | |
| 2016/0315898 | A1* | 10/2016 | Kaplan | G16H 80/00 |
| 2017/0053552 | A1 | 2/2017 | Zhong et al. | |
| 2017/0329908 | A1 | 11/2017 | Braswell | |
| 2018/0197638 | A1 | 7/2018 | Blanshard et al. | |
| 2019/0004692 | A1 | 1/2019 | Mason | |
| 2019/0156937 | A1 | 5/2019 | Shimomura et al. | |
| 2019/0207857 | A1 | 7/2019 | Shelton, IV et al. | |
| 2022/0078829 | A1 | 3/2022 | Bergheim et al. | |
| 2023/0156758 | A1* | 5/2023 | Fan | H04W 72/25 |
| | | | | 370/329 |

FOREIGN PATENT DOCUMENTS

| | | |
|---|---|---|
| JP | 2018032226 | 3/2018 |
| JP | 2019525337 | 9/2019 |
| WO | WO2007058821 | 5/2007 |
| WO | WO2010023409 | 3/2010 |
| WO | WO2012060899 | 5/2012 |
| WO | WO2013134639 | 9/2013 |

OTHER PUBLICATIONS

McGaughey, S. R. "Smart phone based telemedicine system" (Order No. 1517732). Available from ProQuest and Theses Professional. (1027935465). Retrieved from https://dialog.proquest.com/professional/docview/1027935465?accountid=131444 (Year: 2012).

Spok, "Improving Patient Care While Saving Time for Physicians", 10 pages, retrieved on Sep. 28, 2020 from: https://www.spok.com/solutions/healthcare-solutions-role/physicians/#information.

"Integrate Patient Information with Workflow to Deliver Better Patient Care", System Integration and Interoperability, Vocera, 5 pages, retrieved on Sep. 28, 2020 from: https://www.vocera.com/nz/products/integrations-alerts-alarms.

"Adopting Fast Lane in Clinical Communications", Jun. 2017, Cisco Validated Design, PatientSafe Solutions, 29 pages, retrieved from: https://www.cisco.com/c/dam/en/us/td/docs/solutions/CVD/Healthcare/CVD-Adopting-FastLane-Clinical-Comm-PatientSafe-2017JUN.pdf.

Pathinarupothi et al., "Data to diagnosis in global health: a 3P approach", BMC Medical Informatics and Decision Making, 18, Article No. 78 (Sep. 2018), 37 pages, retrieved from: https://bmcmedinformdecismak.biomedcentral.com/articles/10.1186/s12911-018-0568-y.

Spok, "Drive action by connecting clinical teams with the people and information they need when and where it matters most", Clinical Care, 6 pages, retrieved on Sep. 28, 2020 from: https://www.spok.com/solutions/clinical-alerting-notification/.

Philips, Clinical services, Clinical Alarm Management | Philips Healthcare, 6 pages, retrieved by Sep. 28, 2020 from: https://www.philips.co.in/healthcare/clinical-solutions/alarm-management.

"Improving collaboration in healthcare: 5 ways mobile can help", Published May 30, 2019, by Taylor Mallory Holland, retrieved from: https://insights.samsung.com/2019/05/30/improving-collaboration-in-healthcare-5-ways-mobile-can-help.

International Search Report and Written Opinion from International Application No. PCT/US2021/049982, dated Jan. 3, 2022, 9 pages.

\* cited by examiner

200

200

302

304

200

200

200

802

804

1000

Receive From A First Communication Device Associated With A First User A Coverage Request Defining A Coverage Period And Requesting That A Second User Associated With A Second Communication Device Provide Care Coverage For The First User — 1002

Send A Notification Of The Coverage Request To The Second Communication Device Including The Coverage Period And Requesting Agreement To Provide Care Coverage For The First User — 1004

Receive From The Second Communication Device An Acceptance Of The Coverage Request — 1006

Direct To The Second Communication Device A Message Sent To The First Communication Device During The Coverage Period In Response To Receiving The Acceptance Of The Coverage Request — 1008

No

Terminate Coverage Period? — 1010

Yes

Direct Subsequent Messages To First Communication Device — 1012

FIG. 10

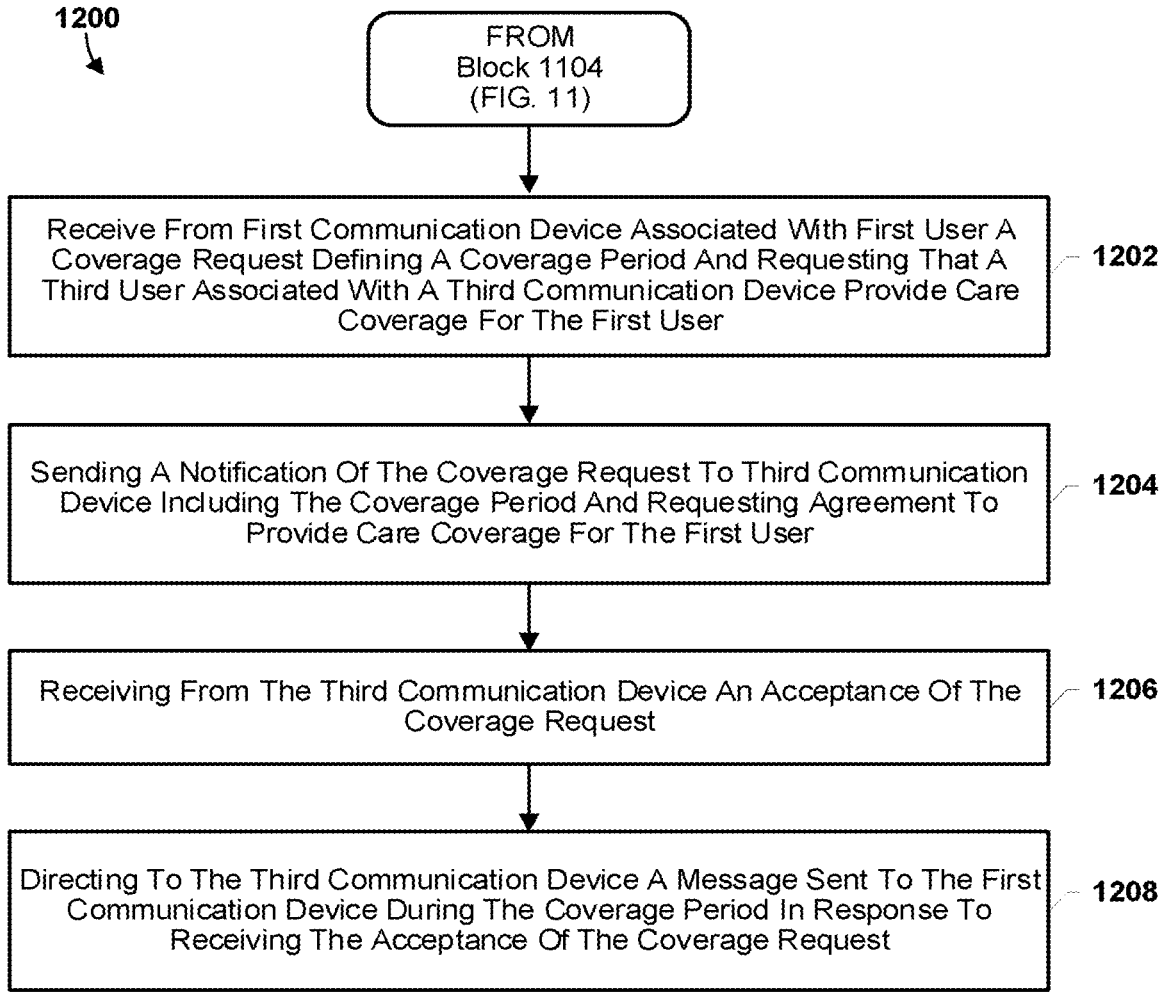

1200

FROM
Block 1104
(FIG. 11)

Receive From First Communication Device Associated With First User A Coverage Request Defining A Coverage Period And Requesting That A Third User Associated With A Third Communication Device Provide Care Coverage For The First User — 1202

Sending A Notification Of The Coverage Request To Third Communication Device Including The Coverage Period And Requesting Agreement To Provide Care Coverage For The First User — 1204

Receiving From The Third Communication Device An Acceptance Of The Coverage Request — 1206

Directing To The Third Communication Device A Message Sent To The First Communication Device During The Coverage Period In Response To Receiving The Acceptance Of The Coverage Request — 1208

FROM
Block 1006
(FIG. 10)

Receive Message From Third Communication Device For The First
Communication Device                                                    1302

Create Conversation Including First Communication Device, Second
Communication Device, And Third Communication Device
From Which Message Was Received                                          1304

Send Received Message To First Communication Device
And To Second Communication Device                                      1306

TO
Block 1010
(FIG. 10)

1400

FROM
Block 1006
(FIG. 10)

Send Instruction To First Communication Device To Mute Notifications
Received By First Communication Device During Coverage Period          1402

TO
Block 1008
(FIG. 10)

1500

FROM
Block 1008
(FIG. 10)

Store Messages Sent To The First Communication Device During The
Coverage Period — 1502

Send Stored Messages To The First Communication Device After The
Coverage Period — 1504

1600

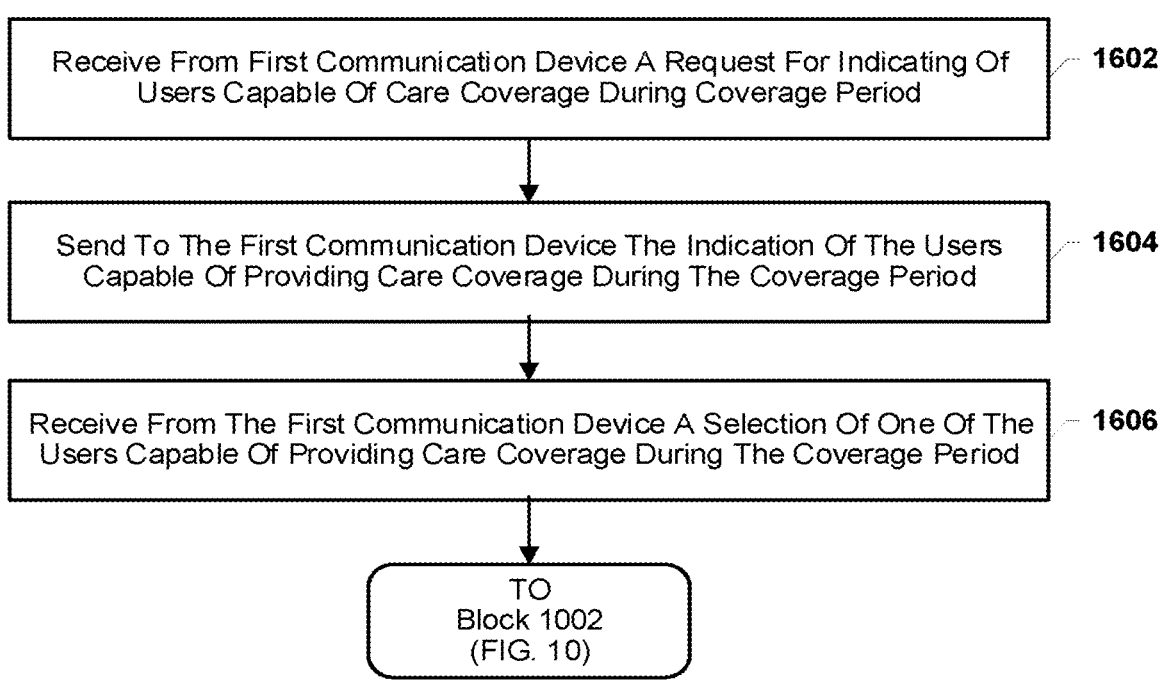

Receive From First Communication Device A Request For Indicating Of Users Capable Of Care Coverage During Coverage Period — 1602

Send To The First Communication Device The Indication Of The Users Capable Of Providing Care Coverage During The Coverage Period — 1604

Receive From The First Communication Device A Selection Of One Of The Users Capable Of Providing Care Coverage During The Coverage Period — 1606

TO
Block 1002
(FIG. 10)

FROM
Block 1008
(FIG. 10)

Receive From First Communication Device A Message Terminating The Coverage Period ⟋ 1702

Direct Subsequent Messages To First Communication In Response To Receiving The Message Terminating The Coverage Period ⟋ 1704

Send A Notification To Second Communication Device Notifying The Second User That The Coverage Period Has Ended ⟋ 1706

CARE PROVIDER COVERAGE FILTER FOR COMMUNICATION DEVICES

REFERENCE TO RELATED APPLICATION

This is a continuation of U.S. patent application Ser. No. 17/024,084, filed Sep. 17, 2020, the entirety of which is hereby incorporated by reference.

BACKGROUND

Distributed communication systems are increasingly utilized to facilitate coordination among workgroups in a variety of environments. Healthcare environments can be busy, information rich, stressful and distracting. Distributed communication systems have proven highly efficacious in hospitals and other healthcare environments, because communication device (which may include mobile communicators, stationary communication terminals, and other suitable communication devices) enable rapid communication among doctors, nurses, and other care team staff who sometimes must provide time-critical patient care.

A care provider may sometimes be occupied by one task and be unable to perform another task, and so the care provider may ask another care provider to perform the other task (i.e., to provide coverage for the other task). In a busy healthcare environment, the process of identifying a care provider capable of providing coverage, determining whether the care provider is available to provide such coverage, and communicating with the requested care provider, can quickly become burdensome. Further, during the period of coverage, it may be distracting to provide messages, alerts, voice calls, etc. to the covered care provider about tasks that the covering care provider is performing.

SUMMARY

Various embodiments provide methods, devices, and non-transitory process-readable storage media for filtering messages, alerts, notifications, and voice calls that are provided to a communication device of a care provider during a period in which another care provider is covering patients or tasks. Various embodiments may include receiving from a first communication device associated with a first user a coverage request defining a coverage period and requesting that a second user associated with a second communication device provide care coverage for the first user, sending a notification of the coverage request to the second communication device including the coverage period and requesting agreement to provide care coverage for the first user, receiving from the second communication device an acceptance of the coverage request, and directing to the second communication device a message sent to the first communication device during the coverage period in response to receiving the acceptance of the coverage request.

Some embodiments may include generating a multi-user conversation data structure including an association between the first communication device and the second communication device. Some embodiments may include determining whether the second user associated with the second communication device has a scheduling conflict during the coverage period. In such embodiments, sending a notification of the coverage request to the second communication device may include sending the notification of the coverage request to the second communication device in response to determining that the second user associated with the second communication device does not have a scheduling conflict during the coverage period.

Some embodiments may include associating a priority with the coverage request, and determining whether the second user associated with the second communication device has a scheduling conflict during the coverage period based in part on the priority associated with the coverage request. Some embodiments may include sending a notification of the scheduling conflict to the first communication device in response to determining that the second user associated with the second communication device has a scheduling conflict during the coverage period. Some embodiments may include sending a notification of the coverage request to a third communication device including the coverage period and requesting agreement of a third user to provide care coverage for the first user in response, receiving from the third communication device an acceptance of the coverage request, and directing to the third communication device a message sent to the first communication device during the coverage period in response receiving the acceptance of the coverage request from the third communication device.

In some embodiments, directing to the second communication device a message sent to the first communication device during the coverage period may include directing to the second communication device a voice call request sent to the first communication device. In some embodiments, directing to the second communication device a message sent to the first communication device during the coverage period may include directing to the second communication device a text-based message sent to the first communication device. In some embodiments, directing to the second communication device a message sent to the first communication device may include creating a conversation including the first communication device, the second communication device, and a third communication device from which the message was received. Some embodiments may include sending an instruction to the first communication device to mute notifications received by the first communication device during the coverage period.

Some embodiments may include storing messages sent to the first communication device during the coverage period, and sending the stored messages to the first communication device after the coverage period. Some embodiments may include receiving from the first communication device a request for an indication of users capable of providing care coverage during the coverage period, sending to the first communication device the indication of the users capable of providing care coverage during the coverage period, and receiving from the first communication device a selection of one of the users capable of providing care coverage during the coverage period. Some embodiments may include receiving from the first communication device a message terminating the coverage period, directing subsequent messages to the first communication device in response to receiving the message terminating the coverage period, and sending a notification to the second communication device notifying the second user that the coverage period has ended. Some embodiments may include receiving a configuration input from the first communication device to tune a type of conversation that will be forwarded to the second communication device when the coverage period is active.

Further embodiments include a server device having a processor configured with processor-executable instructions to perform operations of any of the methods summarized above. Further embodiments include a non-transitory processor-readable medium on which is stored processor-executable instructions configured to cause a processor of a server device to perform operations of any of the methods summarized above. Further embodiments include a server device having means for performing functions of any of the methods summarized above.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

FIGS. 10-17 are process flow diagrams illustrating methods of managing care provider coverage on communication devices according to some embodiments.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 18:
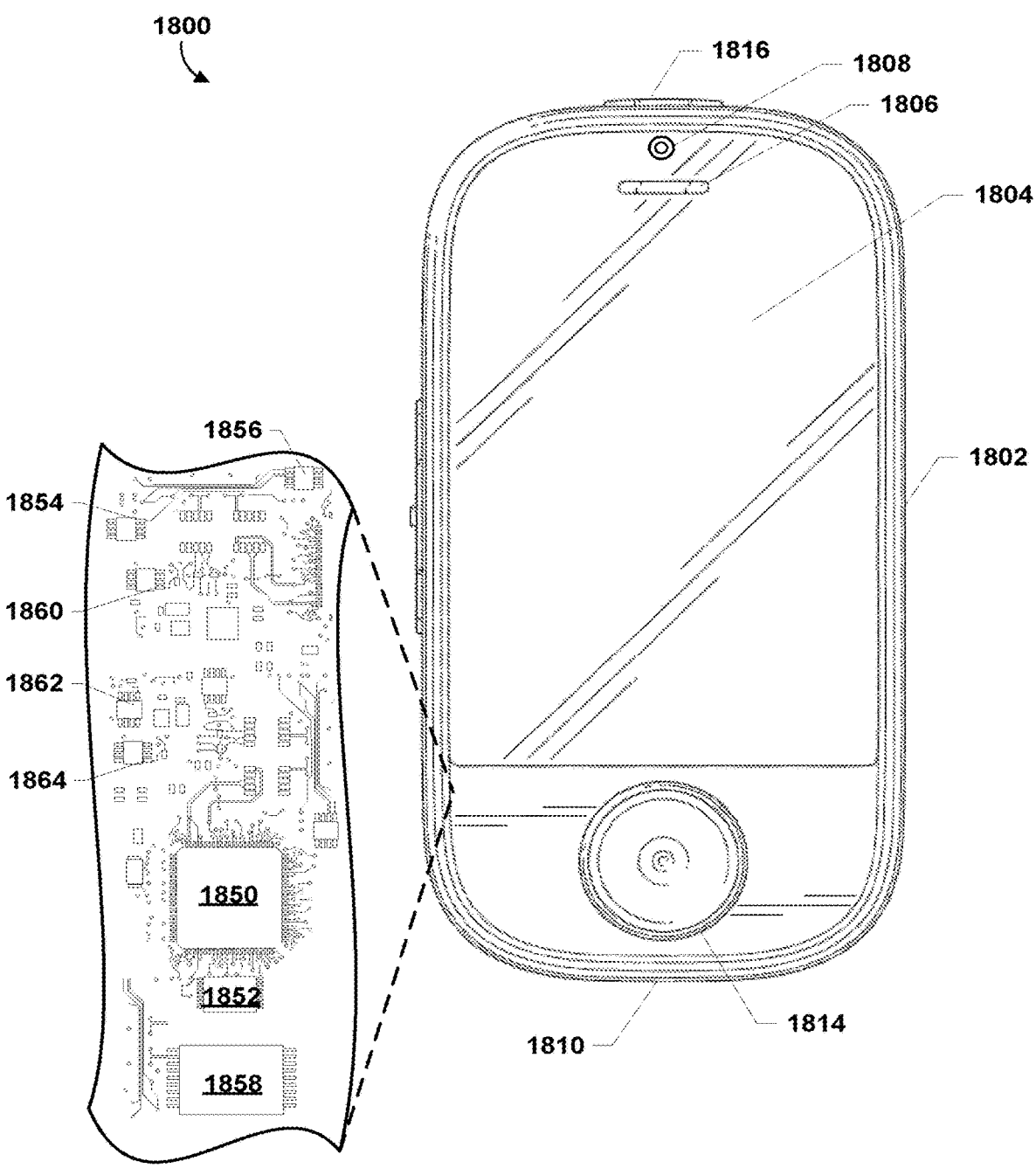
FIG. 18 is a component block diagram of a communication device suitable for use in some embodiments.

The term "communication device" is used herein to refer to an electronic device equipped with at least a processor and an interface configured to enable communication with a communication system or network. Some embodiments may include a wireless communication device equipped with at least a processor and a transceiver configured to support wireless communications with a wireless local area network (WLAN). Examples of communication devices include mobile devices, such as communicators for use within a hospital or other healthcare environments, and stationary or semi-stationary communication devices, such as terminals, surface-mounted communication devices, and other similar communication devices. In various embodiments, communication devices may be configured with memory or storage as well as networking capabilities, such as network transceiver(s) and antenna(s) configured to establish a WLAN connection with an access point. Communication devices may also include voice communications badge devices, an example of which is illustrated in FIG. 18.

The term "covered care provider" is used herein to refer to a care provider for whom a task or responsibility is being performed or monitored. The term "covering care provider" is used herein to refer to a care provider who is performing or monitoring a task or responsibility for the covered care provider.

The term "requesting care provider" is used here in to refer to a care provider who is requesting coverage. The term "requested care provider" is used herein to refer to a care provider who is being requested to provide coverage.

Various embodiments provide methods, devices, and non-transitory process-readable storage media for scheduling coverage for a care provider's patients or tasks and filtering messages that are forwarded to the covered care provider during the time in which the covering care provider cares for patients or performs tasks (referred to herein as a "coverage period"). The terms "message" and "messages" are used herein to refer to alerts, notifications, text-based messages (such as email, instant messages, chat sessions, and the like), voice messages (such as recordings, real-time voice message (such as push-to-talk or "walkie-talkie" style voice transmissions), voice calls (i.e., call requests for a voice communication session), video calls, and other suitable indications of a communication.

It is fairly routine for a care provider to request coverage from another care provider. Certain tasks require the complete attention of the care provider and require the care provider not be interrupted with alerts, messages, or voice calls. For example, discussing a serious illness with a patient, performing a difficult medical task, or speaking with a bereaved relative, each require a period of uninterrupted time during which otherwise routine notifications may affect the quality of care provided. Also, a care provider may request coverage for a more extended period of time, such as while attending to personal matters, work commitments, personal time, etc.

Various embodiments enable the coordination and scheduling of a coverage period during which one or more tasks, one or more patients, and/or other responsibilities of a one care provider (referred to herein as the "covered care provider") is to be performed by another care provider (referred to herein as the "covering care provider"). Various embodiments enable filtering or suppression of messages (or notifications of messages) sent to the communication device of a covered care provider by forwarding messages sent to or intended for the covered care provider to the covering care provider during the coverage period.

In various embodiments, a first user (such as a requesting care provider) may send via a first communication device a request for coverage (a "coverage request") to a second user (a requested care provider) for a defined coverage period of time.

In some embodiments, the first communication device may send to the server device a request for an indication of users capable of providing care coverage during the coverage period. The server device may send to the first communication device the indication of the users capable of providing care coverage during the coverage period, and the first communication device may send to the server device a selection of one of the users capable of providing care coverage during the coverage period (i.e., a selection of the requested care provider).

A server device may receive the coverage request, and send a notification of the coverage request to a second communication device associated with the second user (the requested care provider). The notification may include the coverage period and a request for agreement to provide care coverage for the first user. In some embodiments, the server device may determine whether the second user has a scheduling conflict during the coverage period. In response to determining that the second user does not have a scheduling conflict during the coverage period, the server device may send the notification of the coverage request to the second communication device. In response to determining that the second user does have a scheduling conflict during the coverage period, the server device may send a notification of the scheduling conflict to the first communication device. In some embodiments, the first user may, via the first communication device, identify a third user associated with a third communication device and may send the coverage request for the third user to the server device.

In some embodiments, the server device may receive from the second communication device an acceptance of the coverage request. In response, during the coverage period the server device may direct to the second communication device messages sent to the first communication device. In some embodiments, the server device may send an instruction to the first communication device to mute notifications received by the first communication device during the coverage period.

In some embodiments, the server device may direct to the second communication device a voice call request sent to the first communication device. In some embodiments, the server device may direct to the second communication device a text-based message sent to the first communication device. In some embodiments, the server device may create a conversation including the first communication device, the second communication device, and a third communication device from which the message was received. In some embodiments, generating a conversation may include generating in the server device a data structure that creates a logical linkage among the first, second, or third communication devices that automatically provides to the first, second, and third communication devices a communication sent by one of the first, second, and third communication devices to one of the other communication devices. For example, the server device may automatically direct to the second communication device a text-based message sent by the third communication device to the first communication device. Further, the server device may automatically direct to the first communication device a message (such as a response) sent by the second communication device to the third communication device.

In some embodiments, the server device may store messages sent to the first communication device during the coverage period, and may send the stored messages to the first communication device after the coverage period. In some embodiments, the covered care provider may terminate the coverage period early (i.e., before the end of the defined coverage period). In such embodiments, the first communication device may send to the server device a message terminating the coverage period. In response to receiving the message terminating the coverage period, the server device may direct subsequent messages to the first communication device in response (i.e., may no longer direct messages to the second communication device). The server device may send a notification to the second communication device notifying the second user that the coverage period has ended.

Various embodiments improve the operation of a communication system by automatically filtering potentially distracting messages, alerts, notifications, and voice calls that would otherwise be triggered on the first communication device during the coverage period. Various embodiments improve the operation of a communication system by ensuring that messages vital to patient care are directed to the correct care provider during a coverage period. Various embodiments improve the operation of a communication system by enhancing the speed, relevance, and quality of communication in a stressful, distracting, and information rich environment such as a health care environment. Various embodiments improve the operation of a communication system by reducing the time required to convey relevant and/or time-sensitive information from one communication device to another.

Figure 1:
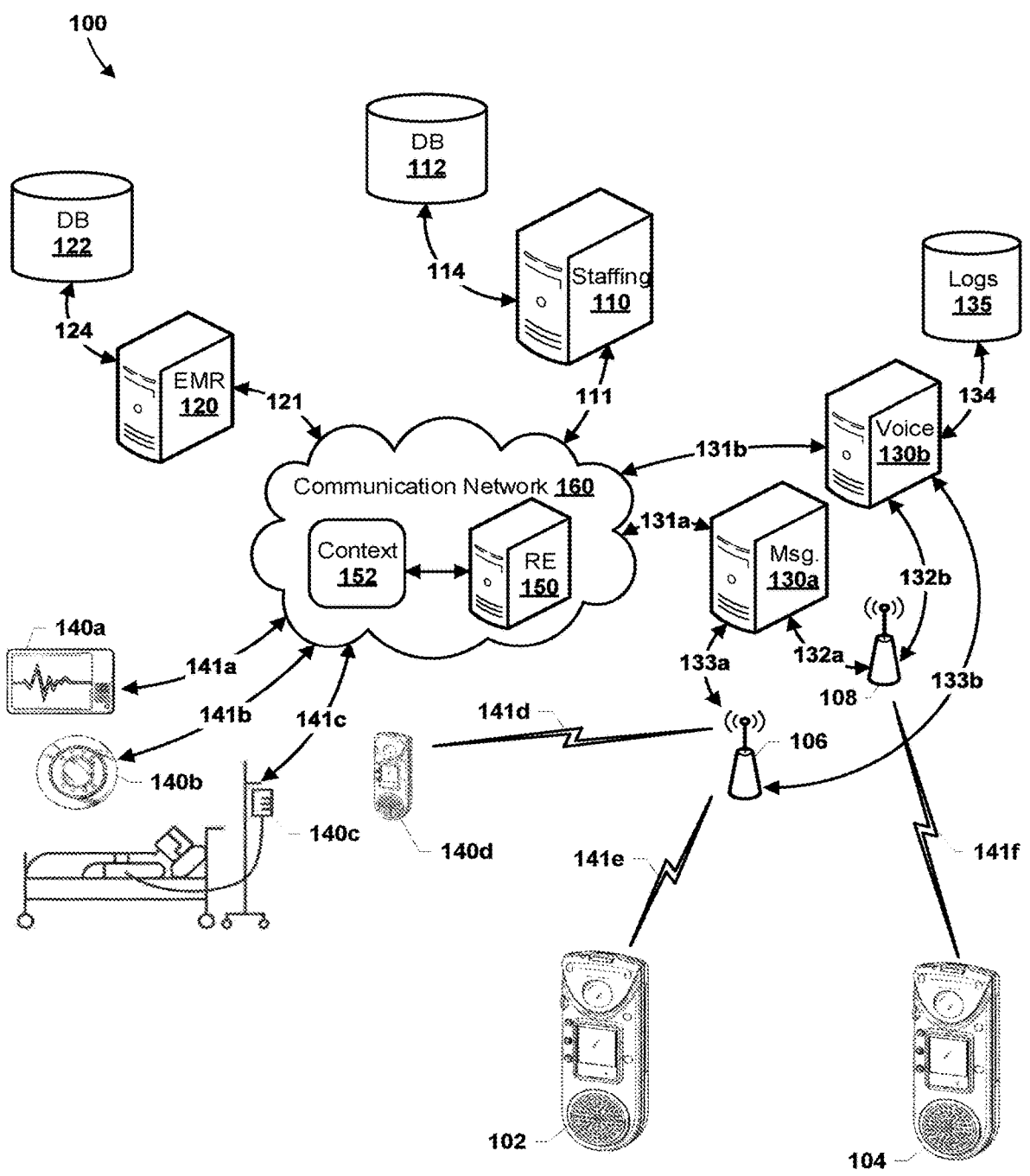
FIG. 1 is a component block diagram of a communication system suitable for use in various embodiments.

FIG. 1 illustrates a communication system 100 suitable for use with the various embodiments. The communication system 100 may include communication devices 102, 104, a staffing server 110, an electronic medical record (EMR) server 120, a messaging server 130a, a voice communications server 130b, one or more sensors/sources 140a-140d, and a rules engine 150. The various elements of the communication system 100 may be configured to communicate over a communication network 160 via wired or wireless communication links 111, 114, 121, 124, 131a, 131b, 132a, 132b, 133a, 133b, and 141a-141f. In some embodiments, one or more of the staffing server 110, the EMR server 120, the messaging server 130a, the voice communications server 130b, and the rules engine 150 may be configured as separate devices (e.g., server devices). In some embodiments, one or more of the staffing server 110, the EMR server 120, the messaging server 130a, the voice communications server 130b, and the rules engine 150 may be configured as separate logical services on one server or similar device.

The EMR server 120 may include one or more server computing devices configured to store, update, and transmit information such as patient-based data. The EMR server 120 may communicate over a wired or wireless communication link 124 with a database 122 configured to store data records. Patient-based data may include identifiers or codes indicating an identity of a patient, health care personnel associated with the patient (e.g., physician, specialist, hospitalist, nurse, etc.), patient location information (e.g., room, bed, wing, building), a status of the patient (e.g., discharged, admitted, etc.), and other suitable information.

The EMR server 120 may transmit messages (e.g., in HL7 or another suitable format) including patient-based data via one or more information feeds. In some embodiments, the EMR server 120 may transmit the messages on the occurrence of an event that changes the patient-based data at the EMR server 120. For example, the EMR server 120 may transmit a message that indicates a patient identifier and a room identifier in response to the patient corresponding to the patient identifier being admitted to the hospital and being assigned to a room corresponding to the room identifier.

In some embodiments, the EMR server 120 may be connected to or otherwise may utilize a system capable of sending and receiving HL7 version 2.3 messages (e.g., admit-discharge-transfer (ADT) messages), such as messages that include a role (or "ROL") segment that indicates care team assignment information. The EMR server 120 may transmit information (e.g., in HL7, ADT messaging, or another suitable format) via one or more information feeds (e.g., to the rules engine 150).

The staffing server 110 may be one or more server computing devices configured to at least synchronize care team assignment data from different systems related to the hospital. The staffing server 110 may communicate over a wired or wireless communication link 114 with a database 112 configured to store data records. The staffing server 110 may transmit information (e.g., in HL7, ADT messaging, or another suitable format) via one or more information feeds (e.g., to the rules engine 150).

In some embodiments, the staffing server 110 may be configured to continually receive data from the EMR server 120, the voice communications server 130b, and/or other systems that indicate staffing changes (e.g., to care teams associated with the various patients, locations, and/or shifts of the hospital). For example, the staffing server 110 may receive subscription messages from the voice communications server 130*b* indicating when particular nurses of the hospital log-in or out of a shift and/or HL7 messages from the EMR server 120 that indicate when a particular patient's data changes (e.g., assigned to a new bed, room, specialist doctor, etc.). The data records may include records related to the various patients admitted to a hospital and/or the various care teams active in the hospital, and may be accessed to obtain a data record indicating the last known nurse, nurse assistant, bed, wing, building, physician, specialist, and hospitalist for a particular patient identifier.

The messaging server 130*a* may include one or more server computing devices configured to control various messages sent between the communication devices 102, 104 via access points 106, 108. In some embodiments, the messaging server 130*a* may be configured to control messages sent to the communication devices 102, 104 from the rules engine 150.

The voice communications server 130*b* may include one or more server computing devices configured to control various voice calls placed between the communication devices 102, 104 via wireless access points 106, 108. In some embodiments, the voice communications server 130*b* may include a signaling gateway service to facilitate communications between and among the communication devices 102, 104 and the voice communications server 130*b*, such as login functions, voice call functions, and other suitable functions. In some embodiments, the signaling gateway service may be configured as a separate device (not illustrated).

As noted above, in various embodiments, the messaging server 130*a* and the voice communications server 130*b* may be configured as separate devices, or as logical functions in one device. In some embodiments, the messaging server 130*a* and the voice communications server 130*b* may transmit information in a suitable format via one or more information feeds (e.g., to the rules engine 150).

In operation, the communication system 100 may include a large number of communication devices and access points, illustrated as communication devices 102, 104, 140*d* and access points 106, 108 for conciseness. The communication devices 102, 104, 140*d* may communicate with an access point 106, 108 over wireless communication links 141*d*-141*f*. The access points 106, 108 may communicate with the voice communications server 130*b* over separate communication links 132*b*, 133*b*. The voice communications server 130*b* may control various messages and voice calls placed between the communication devices 102, 104, 140*d*. The voice communications server 130*b* may communicate over a wired or wireless communication link 134 with a logs database 135 configured to store logs and other data records.

In some embodiments, the voice communications server 130*b* may be configured to provide information to the rules engine 150 via one or more information feeds. For example, the voice communications server 130*b* may store, update, and transmit at least shift-based and/or location-based data of the various care team assignments of the hospital. The voice communications server 130*b* may also store, update, and transmit patient-related information, information related to the facility or environment, and other information. For example, the voice communications server 130*b* may receive messages from any of the communication devices 102, 104, 141*d* that indicate users of the communication devices 102, 104, 141*d* have logged-out of or logged-into a shift of working in a care team at the hospital. As another example, the voice communications server 130*b* may receive a message from a communication device 102, 104, 141*d* regarding the condition of a patient, equipment, a location, an environmental condition, or other suitable information. The voice communications server 130*b* may transmit information in a suitable format via one or more information feeds (e.g., to the rules engine 150).

The one or more sensors/sources 140*a*-140*d* may include one or more sensor devices to sense information about a patient, an environment, or other suitable information. The one or more sensors/sources 140*a*-140*d* may further include one or more sources information about a patient, an environment, or other suitable information, such as a bed exit monitor, a nurse call button/system, a video surveillance system, or another suitable source. For example, patient monitors 140*a*, 140*c* may include devices configured to monitor one or more patient conditions or vital signs. Room sensors 140*b* may be configured to sense and provide information about one or more environmental conditions, or aspects of a person or object to which the sensor is attached (e.g., temperature, humidity, motion, door or window security, ambient light conditions, location, acceleration, orientation, etc.). In some embodiments, the one or more sensors/sources 140*a*-140*d* may transmit information in a suitable format via one or more information feeds to the rules engine 150.

Communication devices 102, 104, 140*d* may also function as a source of clinical or call context information, such as identifying users of the devices (i.e., caregivers) in proximity to a patient. In some embodiments, the one or more sensors/sources 140*a*-140*d* may be configured with, or may communication with a device configured with, a processor and a wired or wireless communication capability to communicate sensed information in a suitable format over wired or wireless communication links 141*a*-141*d*.

The rules engine 150 may include one or more server computing devices configured to receive clinical information via various information feeds from other network elements such as the staffing server 110, the EMR server 120, and the one or more sensors/sources 140*a*-140*d*. In various embodiments, the various network elements (e.g., the staffing server 110, the EMR server 120, and the one or more sensors/sources 140*a*-140*d*) may be configured to send information to the rules engine 150 in an unsolicited manner (e.g., without requiring a query or another message soliciting information).

By receiving information feeds from the other network elements, the rules engine 150 may avoid interfering with or otherwise altering the normal function and efficiency of the other network elements. For example, the rules engine 150 may not alter electronic medical records stored on the EMR server 120, but rather may receive information periodically provided by the EMR server 120 and stored on the rules engine 150.

The rules engine 150 may be configured to associate certain portions or element(s) of the clinical information with one or more event identifiers for use in generating call context information for an event identifier associated with a particular communication request (i.e., call). Further, the rules engine 150 may be configured to provide the call context information to a called communication device 102, 104, e.g., when a communication request is sent to a communication device 102, 104, as further described below.

The communication links 111, 114, 121, 124, 131*a*, 131*b*, 132*a*, 132*b*, 133*a*, 133*b* and 141*a*-141*f* may include wired or wireless communication links. Wired communication links may include, for example, twisted pair cable, coaxial cable or fiber optic cable, or combinations thereof. Wireless communication links may include a radio frequency, microwave, infrared, or other similar signal. Wireless communication links may include a plurality of carrier signals, frequencies, or frequency bands, each of which may include a plurality of logical channels. For example, wireless communication links may be established over a Wi-Fi local area wireless communication network.

Other network elements may be present in a communication system 100 system to facilitate communications are omitted for clarity, including additional access points, processing nodes, routers, gateways, and other network elements, as well as physical and/or wireless data links for carrying signals among the various network elements.

FIGS. 2-8 illustrate operations of a communication device 200 suitable for use in some embodiments. With reference to FIGS. 1-8, the illustrated operations may be implemented in hardware components and/or software components of a communication device (e.g., 102, 104), the operation of which may be controlled by one or more processors of the communication device (a "processor"). In various embodiments, the communication device may communicate with a server device (e.g., 110, 120, 130*a*, 130*b*, 150) to send or receive information relevant to the illustrated operations.

Figure 2:
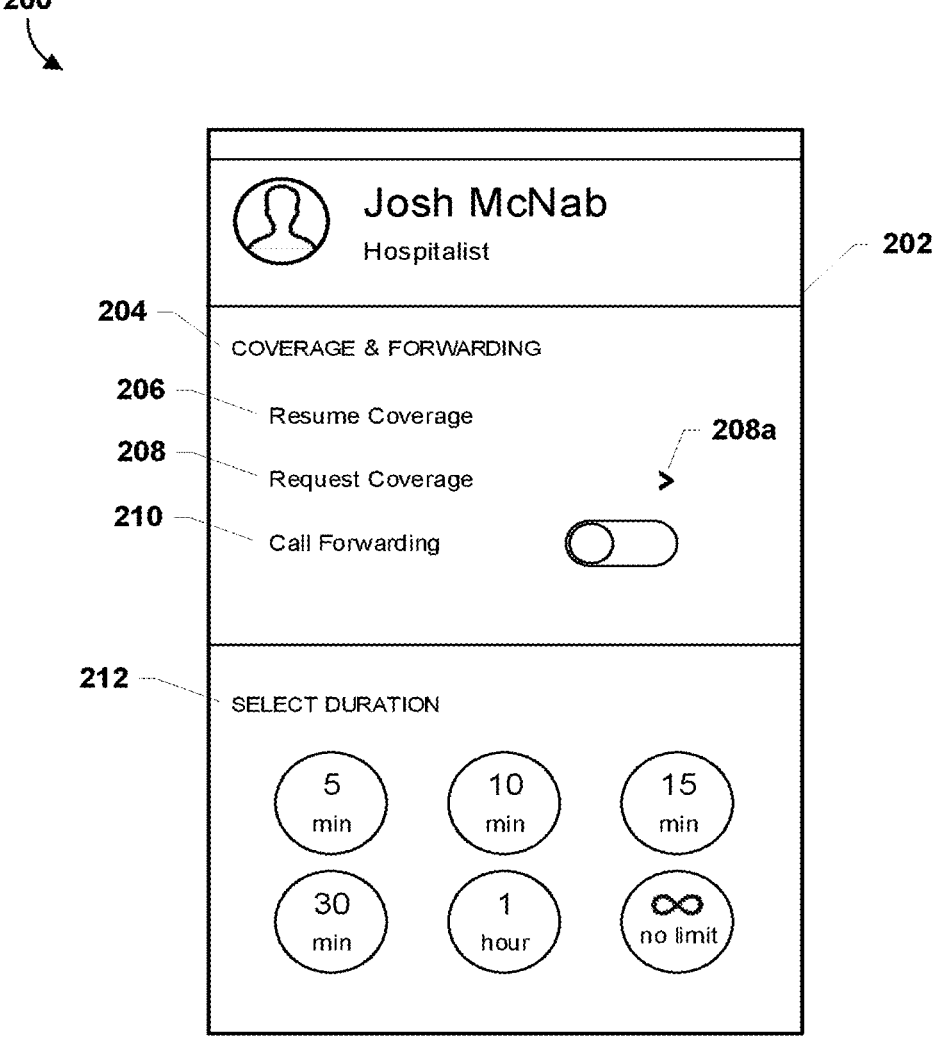
FIGS. 2-8 are examples of user interface displays illustrating operations of a wireless communication device implementing various embodiments.

FIG. 2 illustrates a coverage period definition screen 202 that may be displayed on the communication device 200. The coverage period definition screen 202 may provide options to define a coverage period. For example, the coverage period definition screen 202 may include options 204 for coverage and message forwarding and duration options 212 for the definition of the coverage period. The communication device 200 may be configured to send a message to a server device indicating the selection of one or more of the options.

In some embodiments, the coverage and message forwarding options 204 may include resuming coverage being performed by the user of the communication device 202 (option 206), requesting coverage for the user of the communication device 200 (option 208), and enabling call forwarding of a voice call request sent to the communication device 200 during a coverage period (option 210). The request coverage option 208 may include a function 208*a* that enables a selection of one or more sub-options, such as a coverage time period, a care provider from whom to request coverage, and other suitable sub-options, as further described below.

In some embodiments, the duration options 212 may be presented in a variety of ways. For example, a plurality of time duration options may be presented, as illustrated in FIG. 2. In some embodiments, the duration options 212 may be presented as a slider, dial, wheel, switch, scrollable list (e.g., a "picker"), input field, or another suitable control.

Figure 3:
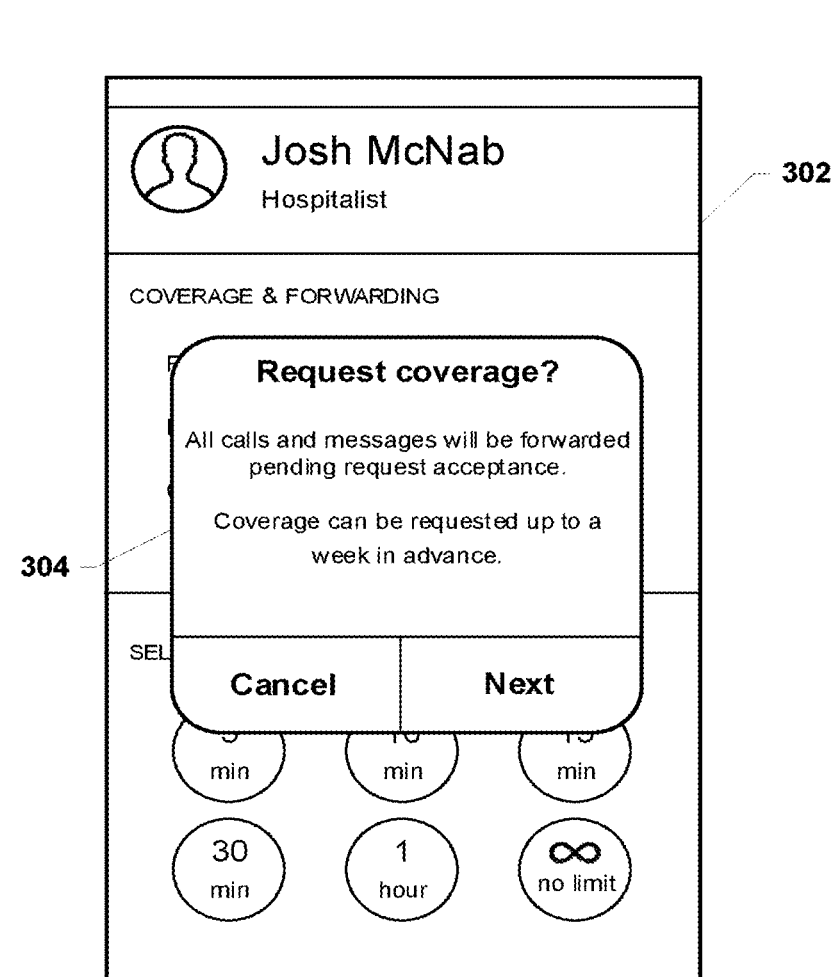

FIG. 3 illustrates a coverage request screen 302 that may be displayed on the communication device 200. In some embodiments, the coverage request screen 302 may include a coverage request function 304 enabling a coverage request to be sent (e.g., "Next" or another suitable function label) or cancelled (e.g., "Cancel").

Figure 4:
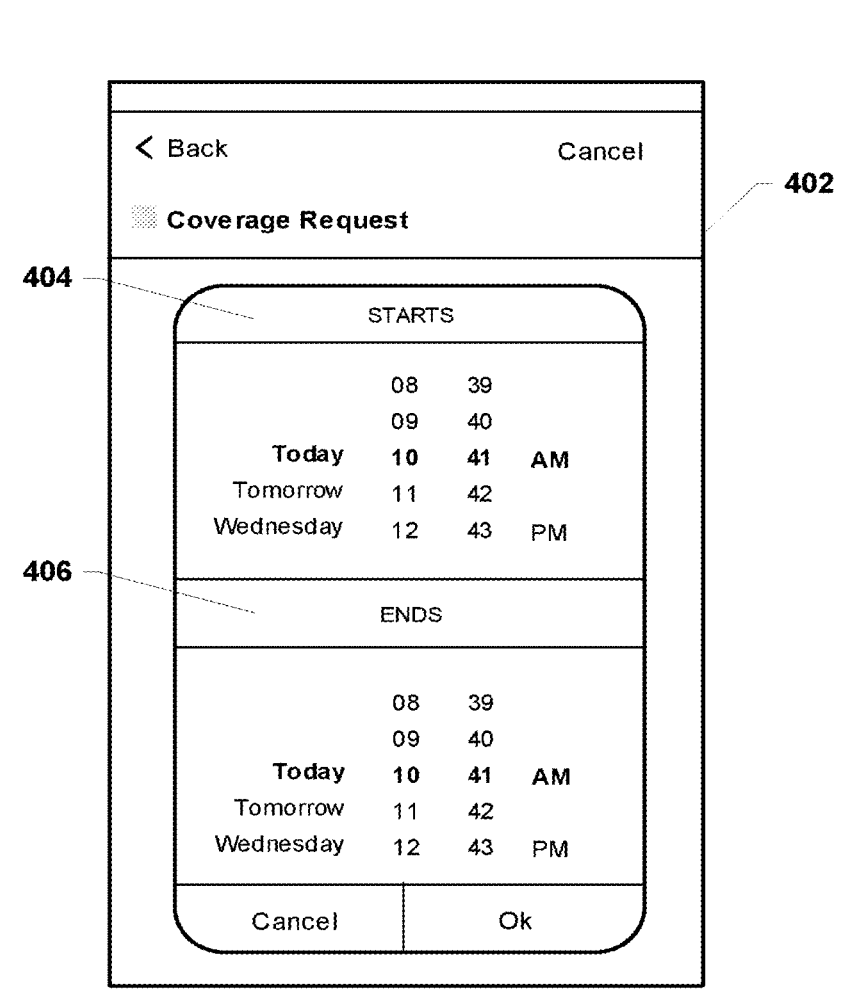

FIG. 4 illustrates a coverage period definition screen 402 displayed on the communication device 200. The coverage period definition screen 402 may include options for defining a start time 404 and an end time 406 of the coverage period. In various embodiments, the start time 404 and end time 406 may be presented as a slider, dial, wheel, switch, scrollable list (e.g., a "picker"), input field, or another suitable control. In some embodiments, the coverage period definition screen 402 may be displayed in response to a selection of the request coverage function 208 or 208*a* (FIG.

2). In some embodiments, the coverage period definition screen 402 may be displayed in response to a selection of the request coverage function 304 (FIG. 3).

Figure 5:
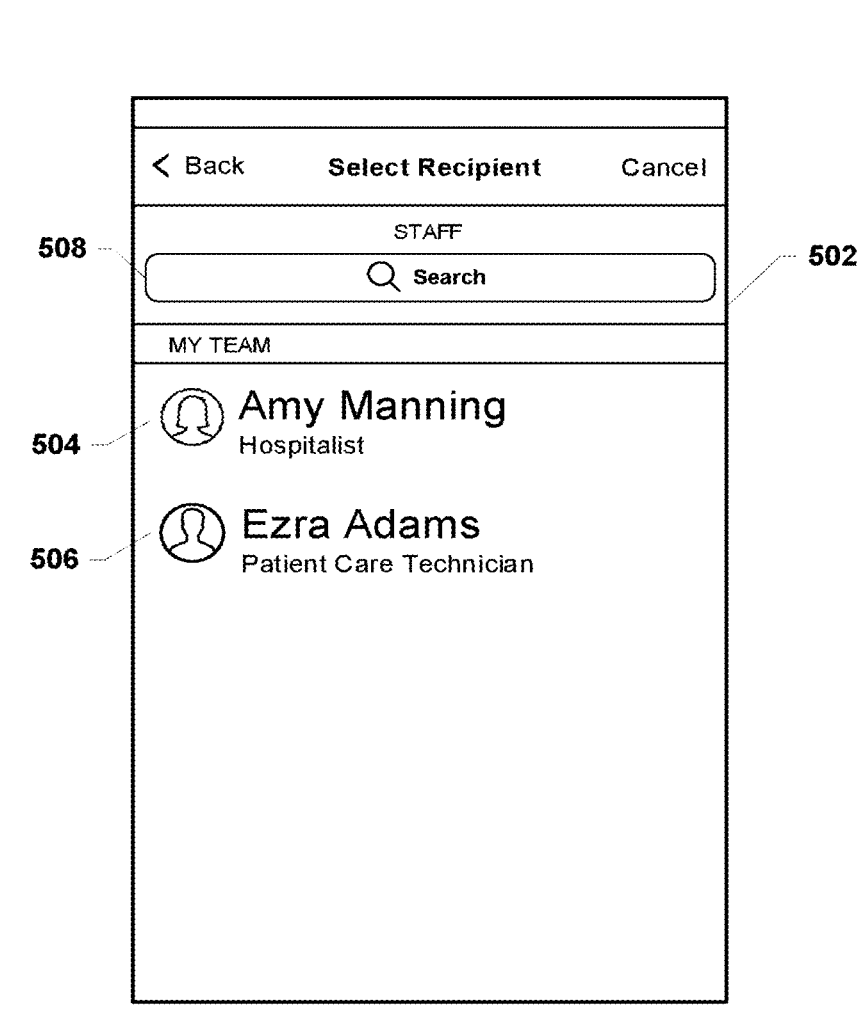

FIG. 5 illustrates a care provider selection screen 502 that may be displayed on the communication device 200. The care provider selection screen 502 may enable the selection of a care provider to whom a request for coverage may be sent (e.g., "Amy Manning," "Ezra Adams," or other suitable options). In some embodiments, the care provider selection screen 502 may be automatically populated with one or more options (504, 506) based on information from the server device. In some embodiments, the care provider selection screen 502 may include a search function 508 that enables a search for a care provider option.

Figures 6A, 6B:
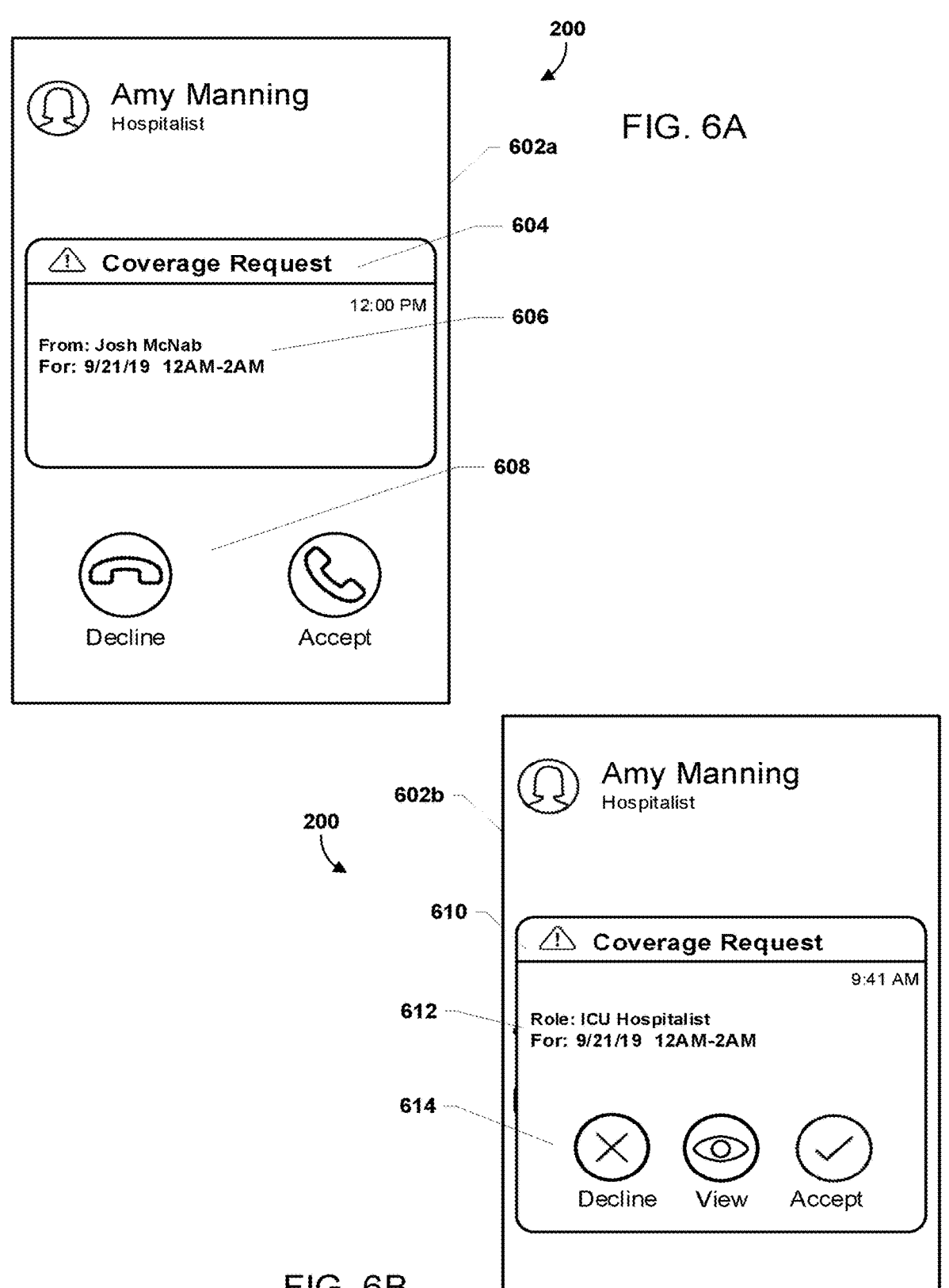

FIGS. 6A and 6B illustrate coverage request alert screens 602*a* and 602*b* that may be displayed on a communication device (e.g., 102, 104, 200) of a recipient of a coverage request (e.g., a second user's communication device). In some embodiments, the recipient may be a recipient selected on the care provider selection screen 502 (e.g., "Amy Manning", option 504, FIG. 5).

Referring to FIG. 6A, the alert screen 602*a* may present an alert 604 in connection with a voice call request from the requesting care provider (e.g., "From: Josh McNab"). The alert 604 may include context information 606 about the request, such as an identification of the sender, the coverage period of the request (e.g., 9/21/19 12 AM-2 AM), or other suitable context information. The alert screen 602*a* may include options 608 to accept or decline the voice call request.

Referring to FIG. 6B, the alert screen 602*b* may present an alert 610 in connection with a text-based request for coverage. The alert 610 may include context information 612 about the request, which may include a role or task of the requested coverage (e.g., "ICU Hospitalist"), the coverage period of the request (e.g., 9/21/19 12 AM-2 AM), or other suitable context information. The alert screen 602*b* may include options 614 to accept or decline the coverage request, to view additional information about the coverage request (e.g., "View"), and/or other suitable options.

Figures 7A, 7B:
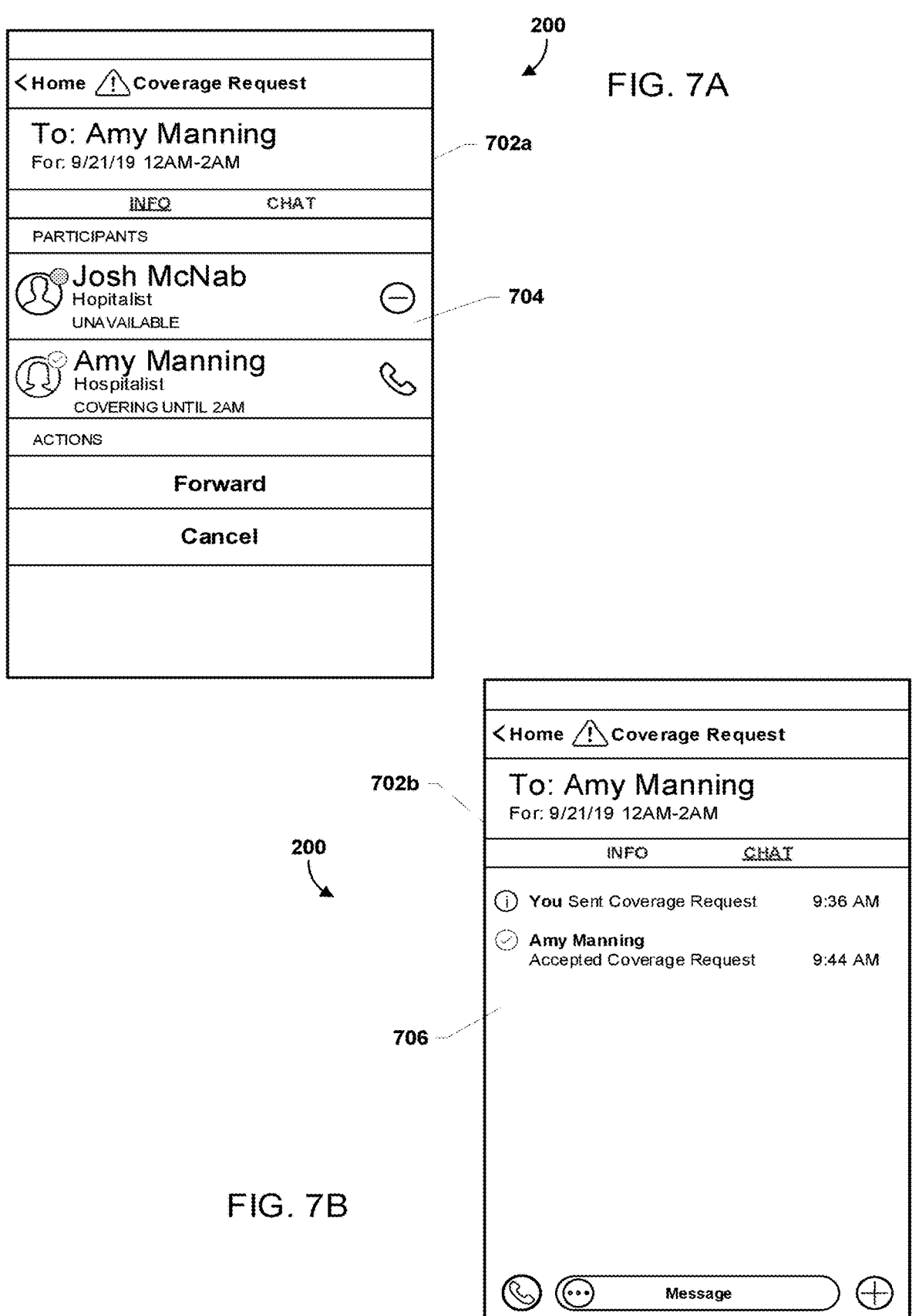

FIGS. 7A and 7B illustrate coverage conversation screens 702*a* and 702*b* that may be displayed on a communication device (e.g., 200). The conversation screens 702*a* and 702*b* illustrate examples of information that may be presented on a covered care provider's communication device (e.g., Josh McNab), but similar information may be presented on a covering care provider's communication device.

In some embodiments, in response to receiving an acceptance of a coverage request, the server may generate a conversation between the covered care provider and the covering care provider. In some embodiments, generating a conversation may include generating in the server device a data structure that creates a logical linkage between the first communication device (associated with the covered care provider) and the second communication device (associated with the covering care provider). The logical linkage may enable messages, alerts, updates, and other information to be sent automatically to the first and second communication devices.

Referring to FIG. 7A, the conversation screen 702*a* may present a listing 704 of participants in the conversation, such as the covered care provider (e.g., "Josh McNab") and the covering care provider (e.g., "Amy Manning") as well as information related to the conversation (e.g., Amy Manning is indicated as "covering until 2 AM".

Referring to FIG. 7B, the conversation screen 702*b* may present a record of events 706 in the conversation, including

| actions performed by one of the communication devices (e.g., sending a coverage request, accepting the coverage request, etc.). The record of events 706 also may include messages sent in the conversation, alerts, notifications, or other information.

Figure 8:
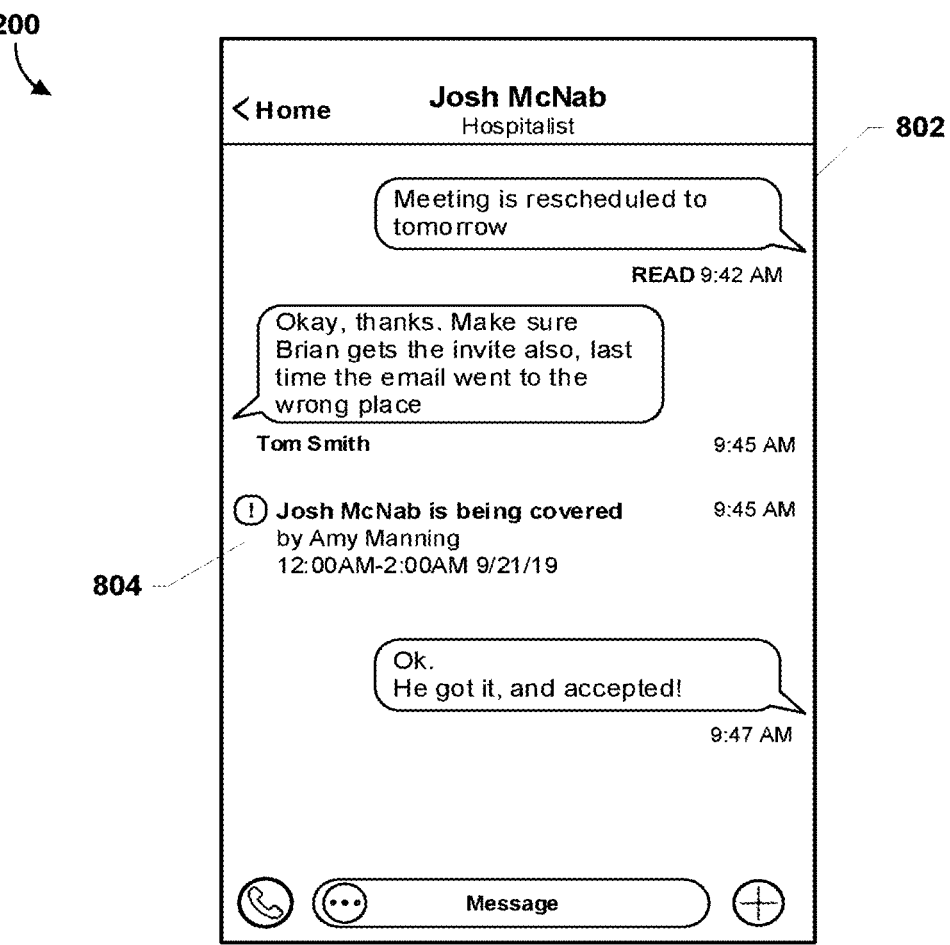

FIG. 8 illustrates a chat screen 802 that may be displayed on a communication device (e.g., 200). The chat screen 802 illustrates an example of information that may be presented on a covered care provider's communication device (e.g., Josh McNab), but similar information may be presented by another communication device, including any participant in a conversation (e.g., a chat session or other text-based messaging) including the covered care provider. The chat screen 802 may include a coverage notification 804 indicating, for example, that the covered care provider (e.g., "Josh McNab") is being covered by the covering care provider (e.g., "Amy Manning"). The coverage notification 804 may serve to notify participants in the text-based messaging session that the covering care provider is now included in the text-based messaging session. The coverage notification 804 also may serve to notify participants that the covered care provider may not immediately receive notifications related to the text-based messaging session, or that notifications may be muted on the covered care provider's communication device.

Figure 9:
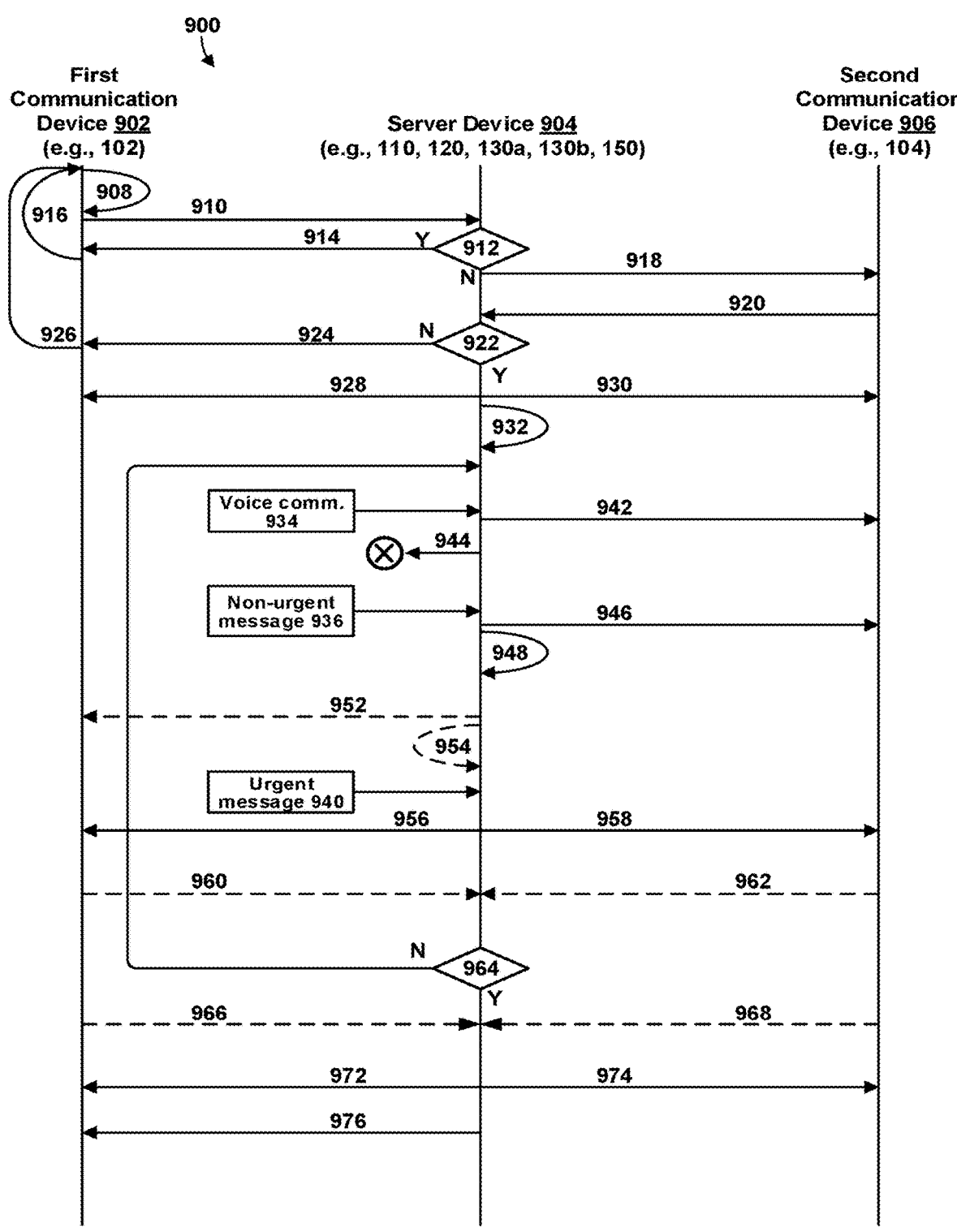
FIG. 9 is a message flow diagram illustrating a method of managing care provider coverage on communication devices according to some embodiments.

FIG. 9 is a message flow diagram 900 illustrating message exchanges and operations of a method of managing care provider coverage via communication devices according to some embodiments. With reference to FIGS. 1-9, the illustrated operations may be implemented in a processor of a first communication device 902, processor of a second communication device 906 (e.g., 102, 104, 200), and a server device 904 (e.g., 110, 120, 130, 150), the operation of which may be controlled by one or more processors.

In operation 908, the processor of the first communication device 902 may generate a coverage request. In some embodiments, generating the coverage request may include defining the coverage period and other parameters of the coverage period, selecting a care provider to receive the coverage request, and other suitable operations. The first communication device 902 may send the coverage request 910 to the server device 904.

In determination operation 912, the server device 904 may determine whether a user associated with the second communication device 906 has a scheduling conflict during the coverage period. In some embodiments, the server device 904 may associate a priority with the coverage request 910. In some embodiments, the server device 904 may determine a priority based on the time at which the coverage request 910 is made and/or the time at which the coverage period is requested to begin. For example, if the duration between the coverage request and the starting time of the coverage period is less than or equal to a designated time period (e.g., 24 hours), the server device 904 may set a priority of the coverage request 910 to "urgent," and if the duration between the coverage request and the starting time of the coverage period is greater than the designated time period (e.g., more than 24 hours in the future), the server device 904 may set the priority of the coverage request 910 to "high." The server device 904 may use the priority associated with the coverage request 910 in evaluating whether the second communication device 906 has a scheduling conflict during the coverage period.

In response to determining that the user associated with the second communication device 906 has a scheduling conflict during the coverage period (i.e., determination operation 912="Y"), the server device 904 may send a response 914 to the first communication device 902 indicating the scheduling conflict.

In operation 916, the first communication device 902 may return to operation 908 and generate a new coverage request for another care provider (e.g., a third care provider associated with a third communication device). In some embodiments, the first communication device 902 may enable the first coverage request to be sent (e.g., forwarded) to the third care provider's communication device.

In response to determining that the user associated with the second communication device 906 does not have a scheduling conflict during the coverage period (i.e., determination operation 912="N"), the server device 904 may send a message 918 including the coverage request to the second communication device 906.

The second communication device may send a response 920 indicating an acceptance or a rejection of the coverage request.

In determination operation 922, the server device 904 may determine whether the response 920 indicates an acceptance of the coverage request. In response to determining that the response 920 does not indicate an acceptance of the coverage request (i.e., determination operation 922="N"), the server device 904 may send a response 924 to the first communication device 902 indicating that the second communication device has declined the coverage request.

In operation 926, the first communication device 902 may return to operation 908 and generate a new coverage request for another care provider (e.g., a third care provider associated with a third communication device). In some embodiments, the first communication device 902 may enable the first coverage request to be sent (e.g., forwarded) to the third care provider's communication device.

In response to determining that the response 920 indicates an acceptance of the coverage request (i.e., determination operation 922="Y"), the server device 904 may send a notification 928 to the first communication device 902 and a notification 930 to the second communication device 906 of the coverage request acceptance. In some embodiments, the notification 928 may include an instruction to the first communication device to mute, silence, or turn off notifications or any messages during the coverage period. "Muting" notifications includes reducing or disabling an announcement of a message, and may include disabling audio notifications, setting a volume of audio notifications, a ringer, or ring tone to zero, disabling a vibration feature or another haptic feedback feature, disabling or reducing visual notifications, or another suitable reduction of similar announcements by the communication device. In some embodiments, the server device 904 may send such instruction to the first communication device 902 in a separate message or signal.

In some embodiments, the server device 904 may generate a data structure including an association between the first communication device 902 and the second communication device 906, such as a "multi-user conversation" (MUC) or another suitable data structure. In some embodiments, the data structure may include an indication for each of the first communication device 902 and the second communication device 906 of a membership level, a level of authorization to make changes to the data structure (e.g., to the MUC), such as an affiliation or another suitable authorization level. For example, the requesting user may be given an "owner" affiliation and the requested user may be given an "administrator" affiliation. In some embodiments, the server device 904 may use the data structure to administer the coverage period, direct messages to the first communication device 902 and the second communication device 906, and perform other determinations. In some embodiments, only users that have been granted membership of room affiliations of owner, administrator, and member are considered members. In some embodiments, a conversation unique identifier (e.g., a Jabber Identifier, or JID) may be prefixed with the string "coverage." Prefixing the JID with a known value may cue the server to reconstitute the conversation after a failover or restart as a coverage conversation. While some of the examples above refer to entities used in the Extensible Messaging and Presence Protocol (XMPP), these examples are not intended to be limiting, and it will be appreciated that other examples and implementations are also possible.

In operation 932, the server device 904 may set an indication in a memory of the server device 904 that the coverage period has begun. In some embodiments, the server device 904 may create a conversation between the first communication device 902 and the second communication device 906 as described.

During the coverage period, various messages sent to the first communication device 902 may be received by the server device 904. Various embodiments enable the service device 904 to evaluate a message received for the first communication device 902 and determine how to handle the received message. For example, depending on an urgency of a message, or a type of message, the server device 904 may: direct the message to the second communication device 904; prevent the message from being directed to the first communication device 902; direct the message to the first communication device 902; join the second communication device 904 to a conversation between the first communication device 902 and a third communication device; send a notification to the first communication device 902 about a received message; store a received message for later forwarding to the first communication device 902; or handle the received message in any variety of ways, including combinations of the foregoing. In some embodiments, a message may be associated with a specific patient (e.g., a "Patient Link Conversation"), may include information to alert a care provider to a particular event or condition (e.g., an "Alert" message), and the like. Any message may be associated with a priority level that reflects an urgency or time-sensitivity of the content of the message.

In some embodiments, the server device 904 may be configured by the inputs received from the first communication device 902 to "tune" the types of conversation(s) that will be forwarded to the second communication device 906 when the coverage period is active. For example, the server device 904 may be configured to forward Patient Link Conversations only, Alerts only, Alerts by priority only, or and number of similar forwarding rules.

In some embodiments, the server device 904 may receive a voice communication request 934 that is sent to the first communication device 902. During the coverage period, the server device 904 may direct the voice communication request 942 to the second communication device 906. In some embodiments, the server device 904 may send an instruction to another server (e.g., the voice communications server 130b) to direct the voice communication request 942 to the second communication device 906. In some embodiments, the server device 904 may prevent the voice communication request 934 from being direct to the first communication device 902 (illustrated in arrow 944). In some embodiments, the server device 904 may send an instruction, e.g., to the voice communications server 130b, to prevent the voice communication request 934 from being direct to the first communication device 902.

In some embodiments, the server device 904 may receive a non-urgent message 936 that is sent to the first communication device 902. In some embodiments, the non-urgent message 936 may include an alert, notification, text-based messages, or another suitable message that does not meet a threshold level of urgency or priority, such as an alert that a diagnostic test result is available, or a non-urgent chat message. During the coverage period, the server device 904 may send a message 946 to direct the non-urgent message 936 to the second communication device 906. In some embodiments, the server device 904 may send a notification 948 to the sender of the non-urgent message 936 (e.g., the sender of the chat message) that the non-urgent message 936 has been directed to the second communication device 906. In some embodiments, the server device 904 may join the second communication device 906 to a conversation between the first communication device 902 and the sender of the non-urgent message 936. In some embodiments, the server device may optionally send a message 952 to the first communication device 902 including the non-urgent message 936. In some embodiments, the message 952 may include an instruction to mute a notification that would otherwise be presented by the first communication device 902. In some embodiments, the server device 904 may optionally store 954 the non-urgent message 936 for later delivery to the first communication device 902.

In some embodiments, the server device 904 may receive an urgent message 940 that is sent to the first communication device 902. In some embodiments, the urgent message 940 may meet a threshold level of urgency or priority, such as a notification of a critical medical emergency or urgent event (e.g., a patient cardiac arrest alert, a fire alert, a hazardous material alert, an evacuation notice, an active shooter notification, and the like). During the coverage period, the server device 904 may send a message 956 to the first communication device 902 including the urgent message 940. The server device 904 also may send a message 958 to the second communication device 906 including the urgent message 940.

Optionally, prior to the end of the coverage period, the first communication device 902 may send a message 960, or the second communication device 906 may send a message 962, to the server device 904 to terminate the coverage period.

Otherwise, in determination operation 964, the server device 904 may determine whether the coverage period has ended. In response to determining that the coverage period has not yet ended (i.e., determination operation 964="N"), the server device may continue to perform operations related to incoming voice communications 934, non-urgent messages 936, and urgent messages 940 as described.

In response to determining that the coverage period has ended (i.e., determination operation 964="Y"), the server device 904 may set an indication in the memory of the server device 904 that the coverage period has ended. Optionally, in order to end the coverage period the server device 904 may require an affirmative action from the first communication device 902 or second communication device 906, such as a message or acknowledgement 966, 968 to avoid a gap in care provider coverage for the covered responsibilities.

The server device 904 may send messages 972 and 974 respectively to the first communication device 902 and the second communication device 906 indicating that the coverage period has ended. In some embodiments, in response to determining that the coverage period has ended (whether it was terminated by a communication device, or expired), the server device 904 may send with the message 972, message 974, or in a separate message, an indication of the device (e.g., 902, 904, 906) that caused or requested the state transition (i.e., the termination or ending of the coverage period). In some embodiments, the server device 904 may expire the conversation and execute all the actions associated with an expired conversation. In some embodiments, the message 972 sent to the first communication device 902 may include a reminder to resume duties, tasks, or activities. For example, when the server discovers an active coverage with a lapsed coverage period and the server hasn't notified the coverage subscribers about this condition since the last restart/failover, the server may send a reminder for the requester to resume coverage.

The server device may send to the first communication device 902 any stored messages 976, such as notifications, alerts, call logs, or any other suitable record or notification of communications that occurred during the coverage period and about which the first communication device 902 has not already been notified.

FIG. 10 is a processor flow diagram illustrating a method 1000 of managing care provider coverage according to some embodiments. With reference to FIGS. 1-10, the illustrated operations may be implemented in hardware components and/or software components of a server device (e.g., 110, 120, 130, 150, 904), the operation of which may be controlled by one or more processors (a "processor").

In block 1002, the processor of the server device may receive from a first communication device associated with a first user a coverage request defining a coverage period and requesting that a second user associated with a second communication device provide care coverage for the first user. In some embodiments, the processor of the server device may generate a data structure including an association between the first communication device and the second communication device. The data structure may include, for example, a MUC or another suitable data structure. In some embodiments, the data structure may include an indication for each of the first communication device and the second communication device of a membership level, a level of authorization to make changes to the MUC, an affiliation, and the like. In some embodiments, the processor of the server device may receive a configuration input from the first communication device to tune a type of conversation that will be forwarded to the second communication device when the coverage period is active. For example, the processor may receive a configuration input indicating that the server device should forward Patient Link Conversations only, Alerts only, Alerts by priority only, etc. when the coverage period is active.

In block 1004, the processor may send a notification of the coverage request to the second communication device including the coverage period and requesting agreement to provide care coverage for the first user.

In block 1006, the processor may receive from the second communication device an acceptance of the coverage request.

In block 1008, the processor may direct to the second communication device a message sent to the first communication device during the coverage period in response to receiving the acceptance of the coverage request. In some embodiments, the processor may direct to the second communication device a voice call request sent to the first communication device. In some embodiments, the processor may direct to the second communication device a text-based message sent to the first communication device.

In determination block 1010, the processor may determine whether to terminate the coverage period. In some embodiments, the processor may terminate the coverage period in response to receiving a termination message from the first or second communication device. In some embodiments, the processor may terminate the coverage period when the coverage time period expires.

In response to determining not to terminate the coverage period (i.e., determination block 1010="No"), the processor may perform the operations of block 1008 as described.

In response to determining to terminate the coverage period (i.e., determination block 1010="Yes"), the processor may direct subsequent messages to the first communication device in block 1012, and the processor may no longer direct messages to the second communication device.

FIGS. 11-17 are process flow diagrams illustrating operations 1100-s1700 that may be performed as part of the method of managing care provider coverage according to some embodiments. With reference to FIGS. 1-17, the illustrated operations may be implemented in hardware components and/or software components of a server device (e.g., 110, 120, 130, 150, 904), the operation of which may be controlled by one or more processors (a "processor").

Figure 11:
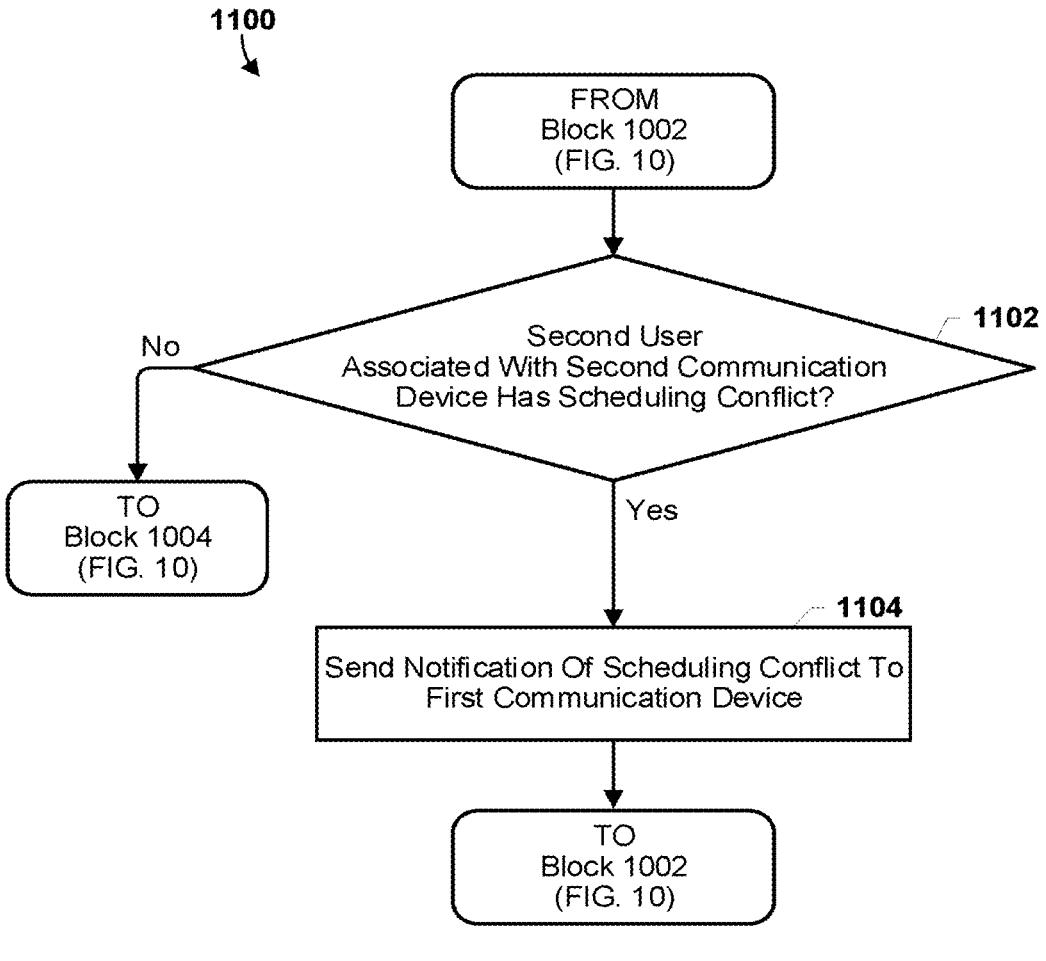

Referring to FIG. 11, following the operations of block 1002 (FIG. 10), the processor may perform operations to determine whether the second user associated with the second communication device has a scheduling conflict in determination block 1102. In some embodiments, this may be accomplished by determining whether the second user has a calendar conflict with the indicated coverage period. In some embodiments, processor may associate a priority with the coverage request, and determine whether the second user associated with the second communication device has a scheduling conflict based in part on the priority associated with the coverage request.

In response to determining that the second user associated with the second communication device does not have a scheduling conflict (i.e., determination block 1102="No"), the processor may proceed to perform the operations of block 1004 (FIG. 10).

In response to determining that the second user associated with the second communication device does have a scheduling conflict (i.e., determination block 1102="Yes"), the processor may send a notification of the scheduling conflict to the first communication device in block 1104.

The processor may then perform the operations of block 1002 as described.

Referring to FIG. 12, following the operations of block 1104 (FIG. 11), the processor may receive from the first communication device associated with the first user a coverage request defining a coverage period and requesting that a third user associated with a third communication device provide care coverage for the first user in block 1202.

In block 1204, the processor may send a notification of the coverage request to a third communication device including the coverage period and requesting agreement of a third user to provide care coverage for the first user in response.

In block 1206, the processor may receive from the third communication device an acceptance of the coverage request.

In block 1208, the processor may direct to the third communication device a message sent to the first communication device during the coverage period in response receiving the acceptance of the coverage request from the third communication device.

Figure 13:
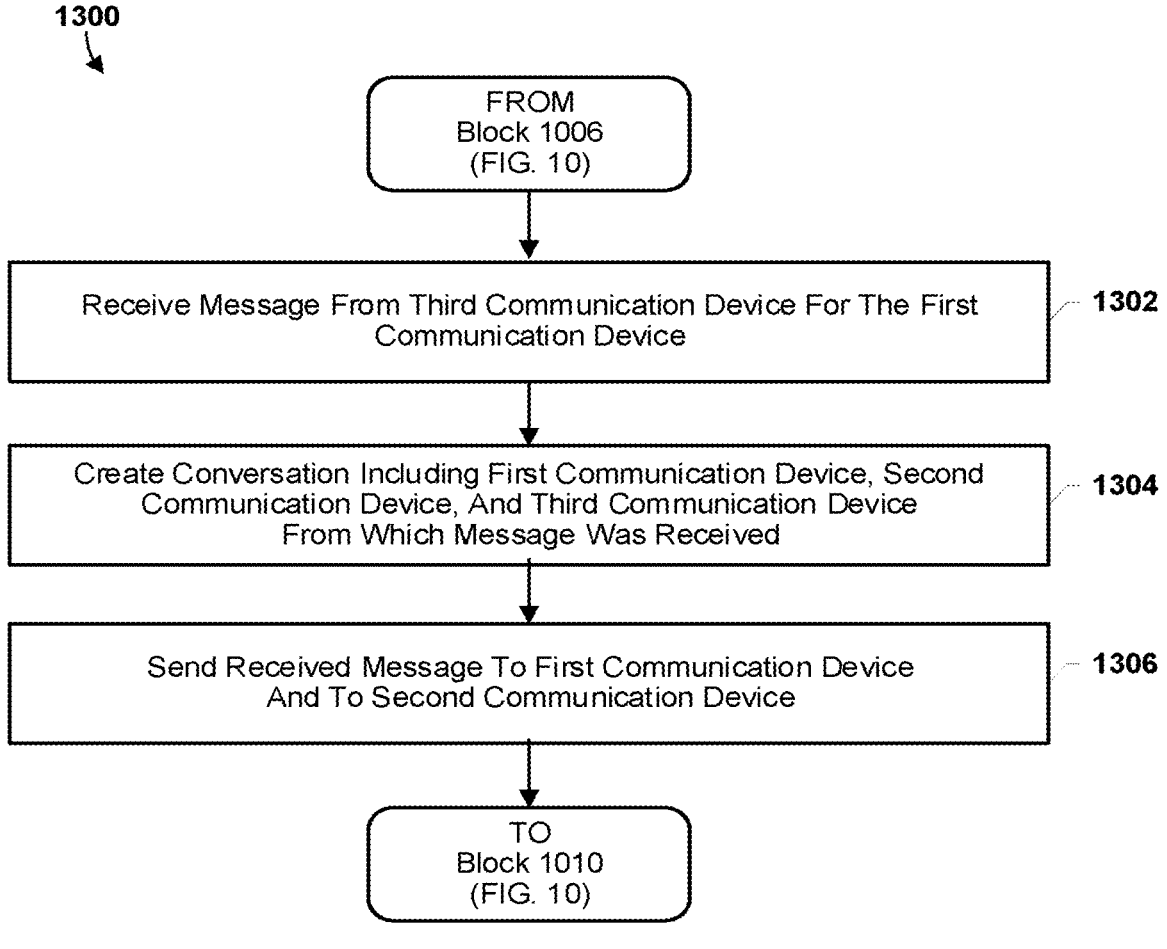

Referring to FIG. 13, following the operations of block 1006 (FIG. 10), the processor may receive a message from a third communication device for the first communication device in block 1302.

In block 1304, the processor may create a conversation including the first communication device, the second communication device, and a third communication device from which the message was received.

In block 1306, the processor may send the received message to the first communication device and the second communication device.

The processor may then perform the operations of block 1010 (FIG. 10) as described.

Figure 14:
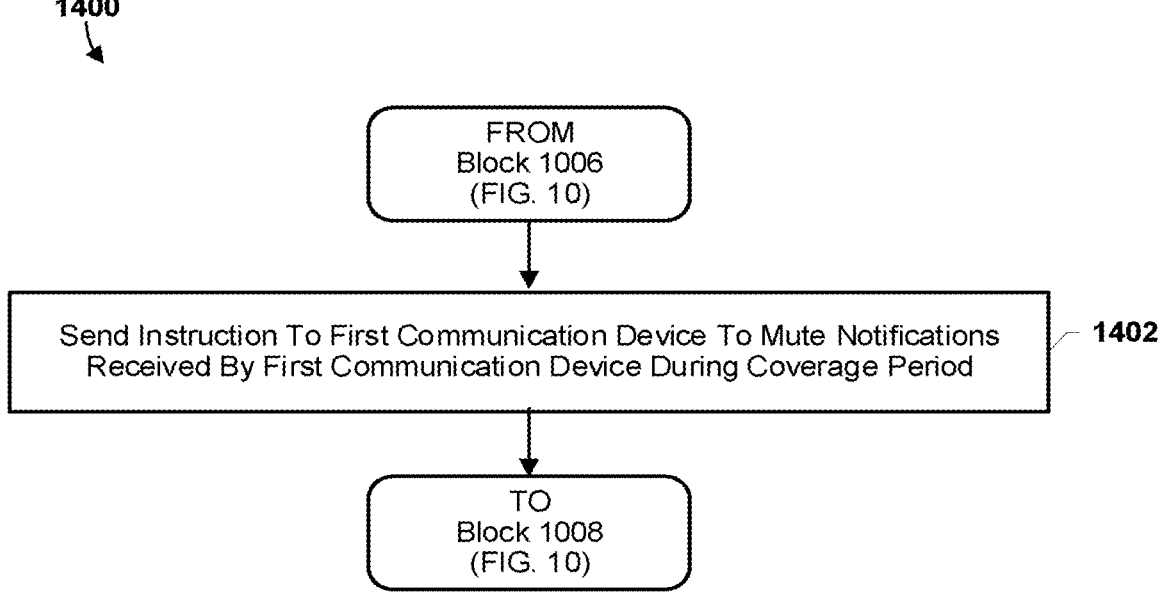

Referring to FIG. 14, following the operations of block 1006 (FIG. 10), the processor may send an instruction to the first communication device to mute notification received by the first communication device during the coverage period in block 1402.

The processor may then perform the operations of block 1008 (FIG. 10) as described.

Figure 15:
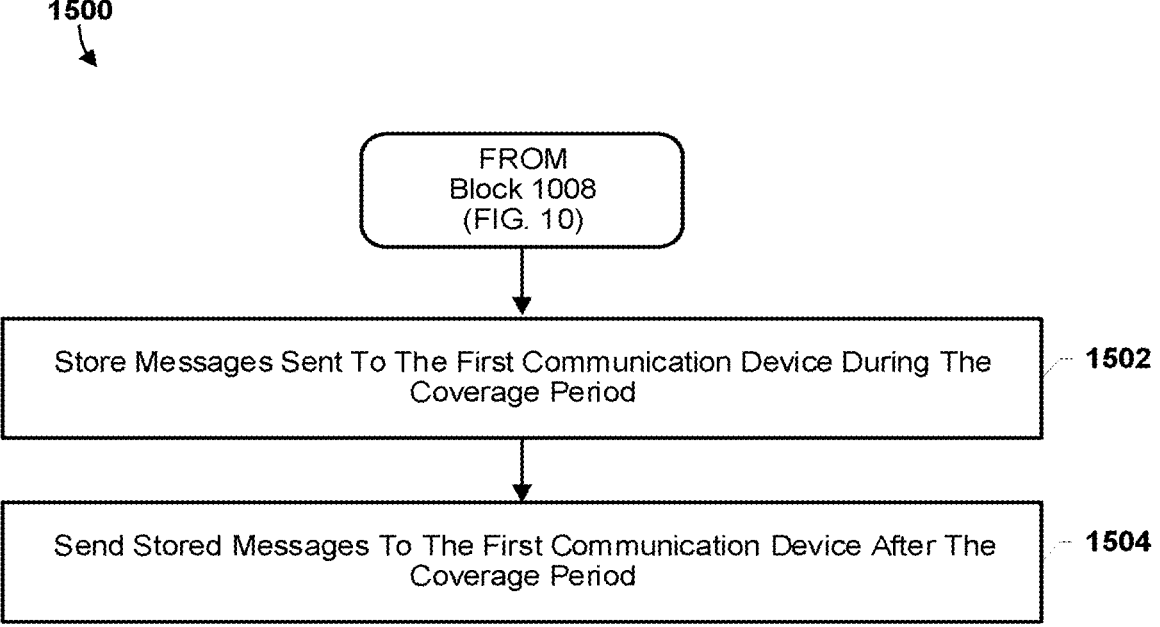

Referring to FIG. 15, following the operations of block 1008 (FIG. 10), the processor may store messages sent to the first communication device during the coverage period in block 1502.

In block 1504, the processor may send the stored messages to the first communication device after the coverage period.

Referring to FIG. 16, prior to the performance of the operations of block 1002 (FIG. 10). the processor may receive from the first communication device a request for an indication of users capable of providing care coverage during the coverage period in block 1602.

In block 1604, the processor may send to the first communication device the indication of the users capable of providing care coverage during the coverage period.

In block 1606, the processor may receive from the first communication device a selection of one of the users capable of providing care coverage during the coverage period.

The processor may then perform the operations of block 1002 (FIG. 10) as described.

Figure 17:
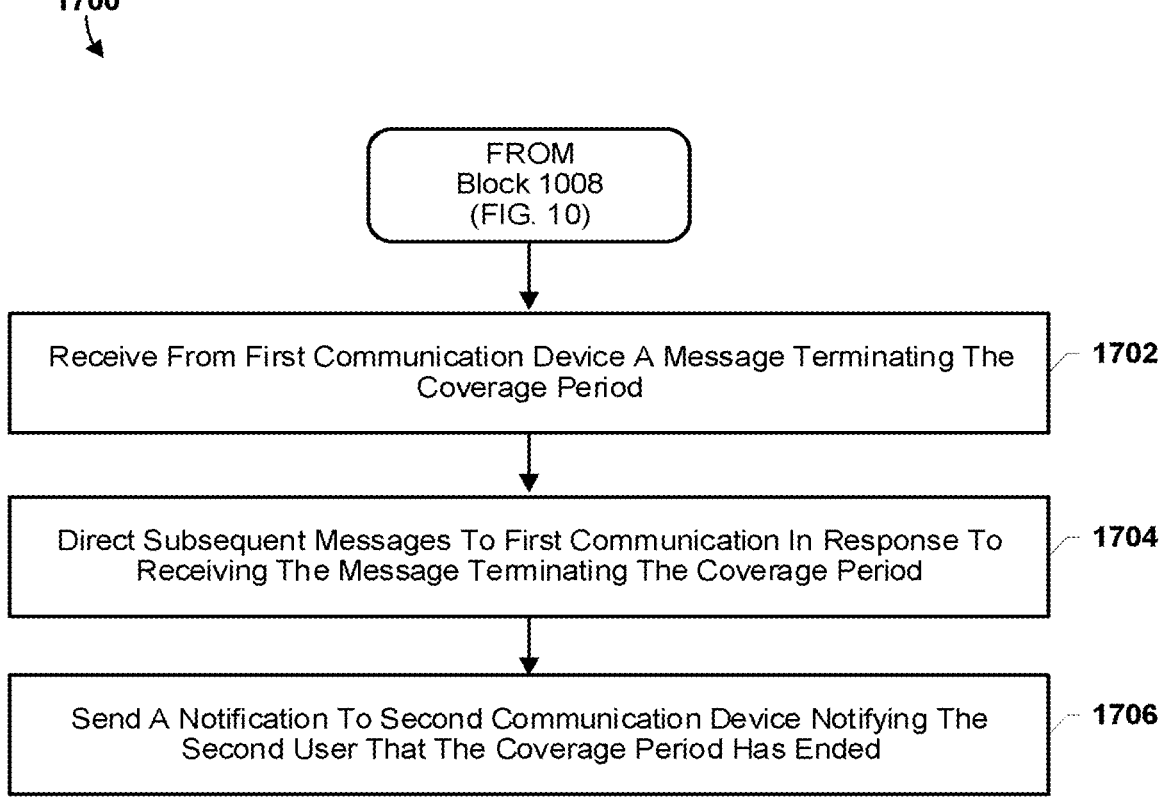

Referring to FIG. 17, following the operations of block 1008 (FIG. 10), the processor may receive from the first communication device a message terminating the coverage period in block 1702.

In block 1704, the processor may direct subsequent messages to the first communication in response to receiving the message terminating the coverage period.

In block 1706, the processor may send a notification to the second communication device notifying the second user that the coverage period has ended.

FIG. 18 illustrates a communication device 1800 suitable for use in various embodiments. With reference to FIGS. 1-18, in some embodiments, the communication device 1800 may include a voice communications badge device. The communication device 1800 may include a housing 1802 that encloses various components. The communication device 1800 may include a microphone 1810, a camera 1808, a speaker 1806, and a display device 1804 such as a liquid crystal display (LCD). Various information may be displayed on the display device 1804, such as data for reviewing text messages and pages received by the communication device 1800 and/or data to facilitate the operation of the communication device 1800. The microphone 1810 and speaker 1806 may also be used for voice communications. In some embodiments, the voice communication device 1800 may further include an amplifier that amplifies the signals provided to/from the microphone and speaker.

The communication device 1800 may further include an input device 1814 that permits a user to configure and operate the communication device 1800. In some embodiments, the input device 1814 may be a jog switch that may be a spring-loaded compound-action switch that supports three momentary actions. In such embodiments, the switch may be pressed inwards as an ordinary push button. In some embodiments, the input device 1814 may also be rotated in either direction and/or may be a touch button location in particular location (e.g., on the front of the communication device 1800) that may be pushed or touched to activate the same functions and operations being activated by the jog switch. The communication device 1800 may also include an on/off switch 1816 and a status indicator, such as a light emitting diode (LED) that may be capable of displaying one or more different colors to signal the operational status of the communication device 1800, etc. In some embodiments, the communication device 1800 may optionally include a headset jack that enables the user to plug in an external microphone/speaker headset, such as an ear bud.

Internally, the communication device 1800 may include a central processing unit (CPU) or processor 1850 that controls the operation of the components of the communication device 1800. For example, the processor 1850 may control the operations of the microphone 1810 and the speaker 1806 so that the communication device 1800 may exchange voice communications, commands, and/or responses with remote devices (e.g., a voice communications server, etc.). The communication device 1800 may further include a non-volatile memory device 1852 so that data stored in the communication device 1800 (such as settings, messages, and other data structures) are not lost when the communication device 1800 is powered down. For example, the non-volatile memory device 1852 may be a storage unit or other memory device configured to store at least a factory-assigned a unique physical media access control (MAC) address or unique wireless device address. The communication device 1800 may also include a wireless transceiver 1854 (e.g., an appropriate strength 802.11 transceiver, etc.) and an antenna 1856 that may be used for wireless communications with various access points or with other devices (e.g., other communication devices, etc.). In some embodiments, the antennae 1856 may be built into an exterior clip of the communication device 1800 or may reside completely within the housing 1802 of the communication device 1800.

The communication device 1800 may further include a pager receiver 1860 that operates with the antenna 1856 to receive text messages/pages within the coverage of any global paging service network. The communication device 1800 may further comprise a digital signal processor (DSP) 1862 and an audio codec 1864 for processing incoming speech from the microphone 1810 and for generating the voice signals generated by the speaker 1806. For example, the DSP 1862 and audio codec 1864 may be capable of compressing digital voice data to reduce the amount of digital data used to communicate the voice commands to the server. The communication device 1800 may include a power source 1858, such as a removable, rechargeable battery that may include protection and charge management circuitry to prevent over-charging. For example, the energy source 1858 may be a replaceable, rechargeable lithium polymer or lithium ion battery that fits on or in the housing 1802. The various components may be connected via a bus or other similar linkage or connectivity.

Exemplary descriptions of various voice communications badge devices suitable for use in various embodiments may also be found in commonly-held patent applications, including U.S. Pat. No. 6,892,083 entitled "Voice-Controlled Wireless Communications System and Method," U.S. Pat. No. 8,098,806 entitled "Non-User-Specific Wireless Communication System and Method," and U.S. Design Pat. No. D679,673, the content of all of which are incorporated herein for descriptions of various communication device components.

Figure 19:
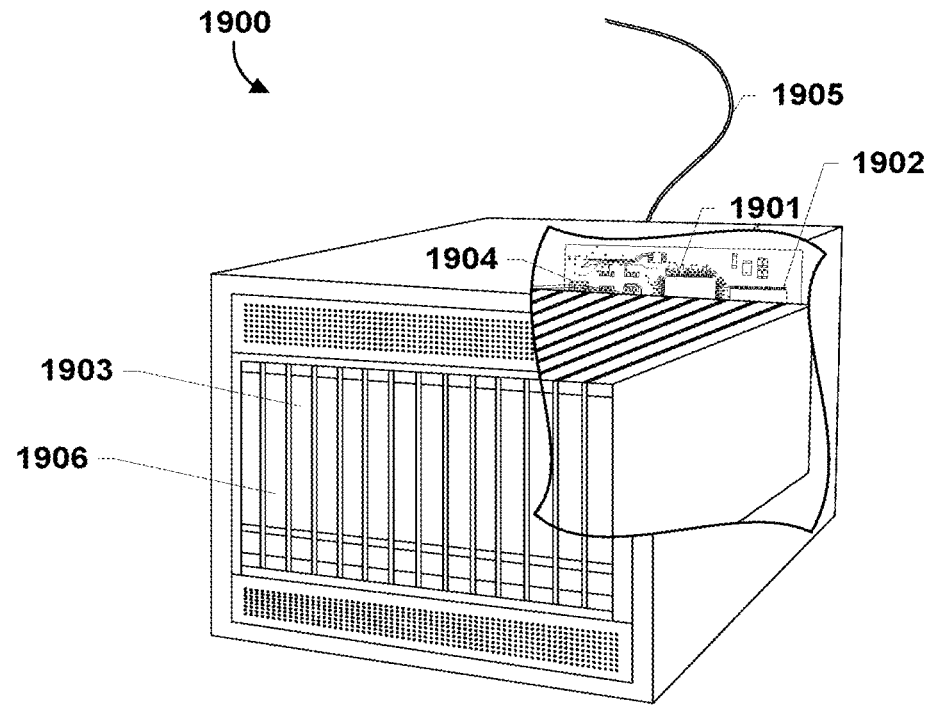
FIG. 19 is a component block diagram of a server computing device suitable for use in some embodiments.

FIG. 19 illustrates a server device 1900 suitable for use in various embodiments. With reference to FIGS. 1-19, various embodiments may employ the server device 1900 as a network element of a communication system (e.g., the communication system 100). Examples of network elements that may be implemented in a server device, or as a logical service in a server device, include the staffing server 110, the EMR server 120, the messaging server 130a, the voice communications server 130b, and the rules engine 150. The server device 1900 may include a processor 1901 coupled to volatile memory 1902 and a large capacity nonvolatile memory, such as a disk drive 1903. The server device 1900 may also include a peripheral memory access device such as a floppy disc drive, compact disc (CD) or digital video disc (DVD) drive 1906 coupled to the processor 1901. The server device 1900 may also include network access ports 1904 (or interfaces) coupled to the processor 1901 for establishing data connections with a network, such as the Internet and/or a local area network coupled to other system computers and servers. The server device 1900 may be coupled via a wired communication link 1905 to one or more wireless access points (e.g., 106, 108). The server device 1900 may include additional access ports, such as USB, Firewire, Thunderbolt, and the like for coupling to peripherals, external memory, or other devices.

The various processors described herein may be any programmable microprocessor, microcomputer or multiple processor chip or chips that can be configured by software instructions (applications) to perform a variety of functions, including the functions of the various embodiments described herein. In the various devices, multiple processors may be provided, such as one processor dedicated to wireless communication functions and one processor dedicated to running other applications. Typically, software applications may be stored in internal memory before they are accessed and loaded into the processors. The processors may include internal memory sufficient to store the application software instructions. In many devices the internal memory may be a volatile or nonvolatile memory, such as flash memory, or a mixture of both. For the purposes of this description, a general reference to memory refers to memory accessible by the processors including internal memory or removable memory plugged into the various devices and memory within the processors.

The foregoing method descriptions and the process flow diagrams are provided merely as illustrative examples and are not intended to require or imply that the operations of the various embodiments must be performed in the order presented. Accordingly, the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical operations, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In one or more exemplary embodiments, the functions described may be implemented in hardware, software, firmware, or any combination thereof. If implemented in software, the functions may be stored on or transmitted over as one or more instructions or code on a non-transitory processor-readable, computer-readable, or server-readable medium or a non-transitory processor-readable storage medium. The operations of a method or algorithm disclosed herein may be embodied in a processor-executable software module or processor-executable software instructions which may reside on a non-transitory computer-readable storage medium, a non-transitory server-readable storage medium, and/or a non-transitory processor-readable storage medium. In various embodiments, such instructions may be stored processor-executable instructions or stored processor-executable software instructions. Tangible, non-transitory computer-readable storage media may be any available media that may be accessed by a computer. By way of example, and not limitation, such non-transitory computer-readable media may comprise RAM, ROM, EEPROM, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of non-transitory computer-readable media. Additionally, the operations of a method or algorithm may reside as one or any combination or set of codes and/or instructions on a tangible, non-transitory processor-readable storage medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method for controlling communication in a healthcare communication system, the healthcare communication system including a plurality of caregiver communication devices each associated with a respective caregiver, the plurality of caregiver communication devices including a first caregiver communication device associated with a first caregiver and a second caregiver communication device associated with a second caregiver, the method comprising:

receiving into a computing system, from the first caregiver communication device, a communication-forwarding request that requests forwarding to the second caregiver communication device, for a defined time period, of communications that are directed to the first caregiver communication device; and based on the communication-forwarding request, the computing system operating for the defined time period in a communication-forwarding mode, wherein operating for the defined time period in the communication-forwarding mode based on the communication-forwarding request comprises (i) for the defined time period, forwarding to the second caregiver communication device communications directed to the first caregiver communication device and (ii) controlling during the defined time period, based on a priority level of a given one of the communications subject to the forwarding, whether to send the given communication to the first caregiver communication device in addition to forwarding the given communication to the second caregiver communication device.

2. The method of claim 1, wherein forwarding to the second caregiver communication device a given one of the communications directed to the first caregiver communication device comprises:

receiving into a server device the given communication directed to the first caregiver communication device; and forwarding the received communication from the server device to the second caregiver communication device.

3. The method of claim 1, wherein forwarding to the second caregiver communication device a given one of the communications directed to the first caregiver communication device comprises:

receiving into a server device the given communication directed to the first caregiver communication device; and forwarding the received communication from the server device to the second caregiver communication device rather than sending the received communication to the first caregiver communication device.

4. The method of claim 1, wherein forwarding to the second caregiver communication device a given one of the communications directed to the first caregiver communication device is conditioned on the given communication being associated with a particular patient.

5. The method of claim 1, wherein a given one of the communications directed to the first caregiver communication device is from a sender, and wherein operating for the defined time period in the communication-forwarding mode in response to the communication-forwarding request further comprises:

sending to the sender of the given communication a notification that the communication has been forwarded to the second caregiver communication device.

6. The method of claim 1, wherein controlling during the defined time period, based on the priority level of the given communication, whether to send the given communication to the first caregiver communication device in addition to forwarding the given communication to the second caregiver communication device comprises:

making a determination of whether the given communication is urgent;

if the determination is affirmative, then sending the given communication to the first caregiver communication device during the defined time period in addition to forwarding the given communication to the second caregiver communication device; and if the determination is negative, then forgoing from sending the given communication to the first caregiver communication device during the defined time period.

7. The method of claim 1, wherein operating for the defined time period in the communication-forwarding mode in response to the communication-forwarding request further comprises:

sending to the first caregiver communication device an instruction to mute notifications received by the first caregiver communication device for a duration of the defined time period.

8. The method of claim 1, further comprising:

upon expiration of the defined time period, sending by the computing system to the first caregiver communication device a notification of one or more communications that were forwarded to the second caregiver communication device during the defined time period.

9. The method of claim 1, wherein receiving the communication-forwarding request from the first caregiver communication device occurs within a week in advance of a start of the defined time period.

10. A computing system comprising:

a processor;

non-transitory data storage; and program instructions stored in the non-transitory data storage and executable by the processor to carry out operations for controlling communication in a healthcare communication system, the healthcare communication system including a plurality of caregiver communication devices each associated with a respective caregiver, the plurality of caregiver communication devices including a first caregiver communication device associated with a first caregiver and a second caregiver communication device associated with a second caregiver, the operations including:

receiving, from the first caregiver communication device, a communication-forwarding request that requests forwarding to the second caregiver communication device, for a defined time period, of communications that are directed to the first caregiver communication device, and

based on the communication-forwarding request, operating for the defined time period in a communication-forwarding mode, wherein operating for the defined time period in the communication-forwarding mode based on the communication-forwarding request comprises (i) for the defined time period, forwarding to the second caregiver communication device communications directed to the first caregiver communication device and (ii) controlling during the defined time period, based on a priority level of a given one of the communications subject to the forwarding, whether to send the given communication to the first caregiver communication device in addition to forwarding the given communication to the second caregiver communication device.

11. The computing system of claim 10, wherein forwarding to the second caregiver communication device a given one of the communications directed to the first caregiver communication device comprises:

receiving the given communication directed to the first caregiver communication device; and forwarding the received communication from the server device to the second caregiver communication device.

12. The computing system of claim 10, wherein forwarding to the second caregiver communication device a given one of the communications directed to the first caregiver communication device comprises:

receiving the given communication directed to the first caregiver communication device; and forwarding the received communication from the server device to the second caregiver communication device rather than sending the received communication to the first caregiver communication device.

13. The computing system of claim 10, wherein forwarding to the second caregiver communication device a given one of the communications directed to the first caregiver communication device is conditioned on the given communication being associated with a particular patient.

14. The computing system of claim 10, wherein a given one of the communications directed to the first caregiver communication device is from a sender, and wherein operating for the defined time period in the communication-forwarding mode in response to the communication-forwarding request further comprises:

sending to the sender of the given communication a notification that the communication has been forwarded to the second caregiver communication device.

15. The computing system of claim 10, wherein controlling during the defined time period, based on the priority level of the given communication, whether to send the given communication to the first caregiver communication device in addition to forwarding the given communication to the second caregiver communication device comprises:

making a determination of whether the given communication is urgent;

if the determination is affirmative, then sending the given communication to the first caregiver communication device during the defined time period in addition to forwarding the given communication to the second caregiver communication device; and if the determination is negative, then forgoing from sending the given communication to the first caregiver communication device during the defined time period.

16. The computing of claim 10, wherein operating for the defined time period in the communication-forwarding mode in response to the communication-forwarding request further comprises:

sending to the first caregiver communication device an instruction to mute notifications received by the first caregiver communication device for a duration of the defined time period.

17. The computing system of claim 10, wherein the operations additionally include:

upon expiration of the defined time period, sending to the first caregiver communication device a notification of one or more communications that were forwarded to the second caregiver communication device during the defined time period.

18. The computing system of claim 10, wherein receiving the communication-forwarding request from the first caregiver communication device occurs within a week in advance of a start of the defined time period.

19. A non-transitory processor-readable medium having stored thereon processor-executable instructions configured to cause a computing system to carry out operations for controlling communication in a healthcare communication system, the healthcare communication system including a plurality of caregiver communication devices each associated with a respective caregiver, the plurality of caregiver communication devices including a first caregiver communication device associated with a first caregiver and a second caregiver communication device associated with a second caregiver, the operations comprising:

receiving, from the first caregiver communication device, a communication-forwarding request that requests forwarding to the second caregiver communication device, for a defined time period, of communications that are directed to the first caregiver communication device; and based on the communication-forwarding request, operating for the defined time period in a communication-forwarding mode, wherein operating for the defined time period in the communication-forwarding mode based on the communication-forwarding request comprises (i) for the defined time period, forwarding to the second caregiver communication device communications directed to the first caregiver communication device and (ii) controlling during the defined time period, based on a priority level of a given one of the communications subject to the forwarding, whether to send the given communication to the first caregiver communication device in addition to forwarding the given communication to the second caregiver communication device.

20. The non-transitory processor-readable medium of claim 19, wherein controlling during the defined time period, based on the priority level of the given communication, whether to send the given communication to the first caregiver communication device in addition to forwarding the given communication to the second caregiver communication device comprises:

making a determination of whether the given communication is urgent;

if the determination is affirmative, then sending the given communication to the first caregiver communication device during the defined time period in addition to forwarding the given communication to the second caregiver communication device; and if the determination is negative, then forgoing from send-
ing the given communication to the first caregiver
communication device during the defined time period.

\* \* \* \* \*